Figure 1:
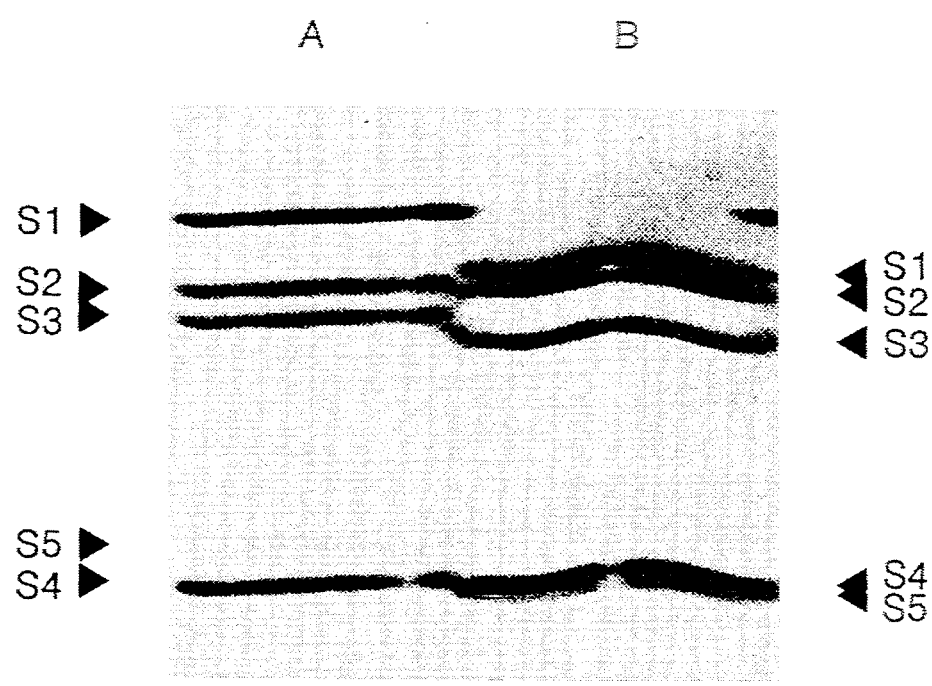

United States Patent [19]

Rappuoli et al.

[11] Patent Number: 5,427,788
[45] Date of Patent: Jun. 27, 1995

[54] PERTUSSIS TOXIN AND USE IN VACCINES

[75] Inventors: Rino Rappuoli, Quercegrossa-Monteriggioni; Alfredo Nicosia, Siena; Maria B. Arico', Quercegrossa, all of Italy

[73] Assignee: Sclavo S.p.A., Siena, Italy

[21] Appl. No.: 261,743

[22] Filed: Jun. 17, 1994

Related U.S. Application Data

[60] Division of Ser. No. 968,162, Oct. 29, 1992, abandoned, which is a continuation of Ser. No. 634,100, Dec. 26, 1990, abandoned, which is a continuation of Ser. No. 6,438, Jan. 23, 1987, abandoned.

[30] Foreign Application Priority Data

Jan. 28, 1986 [IT] Italy .................. 19208/86
Jul. 30, 1986 [IT] Italy .................. 21314/86

[51] Int. Cl.⁶ .................................. A61K 39/10
[52] U.S. Cl. .......................... 424/190.1; 424/240.1; 424/254.1; 514/12
[58] Field of Search ............... 514/12; 435/193, 69.1; 424/190.1, 240.1, 254.1

[56] References Cited

U.S. PATENT DOCUMENTS 4,887,761 11/1989 Keith et al. .................. 435/320

OTHER PUBLICATIONS

Semina et al. (1983) Chem. Abst. 99:170610k.
Weiss et al. (1983) "Infection and Immunity," vol. 42, No. 1, pp. 33–41.
Tamura et al. (1982) Biochemistry 21, pp. 5516–5522.
Capiau et al. (1986) FEBS Letts., vol. 204, pp. 336–340.
Hewlett et al. (1983) "Infection & Immunity," vol. 40, No. 3, pp. 1198–1203.
Sekura et al. (1983) J. Bio. Chem., vol. 258 pp. 14647–14651.
Locht et al. (1986) Science, vol. 232, pp. 1258–1264.
Locht et al. (1986) Nucleic Acids Res., vol. 14, pp. 3251–3261.
Nicosia et al. (1986) Proc. Nat. Acad. Sci., vol. 83, pp. 4631–4635.

*Primary Examiner*—Charles L. Patterson, Jr.
*Attorney, Agent, or Firm*—Barbara G. McClung; Francis A. Paintin

[57] ABSTRACT

Cloning and sequencing of the Eco RI fragment of *B. pertussis* chromosomal DNA with 4696 base pairs, containing the genes which code for the five subunits of the *pertussis* toxin.

A hybrid plasmid containing the DNA fragment or its further fragments and a micro-organism transformed by the hybrid plasmid and capable of expressing the cloned DNA fragment or further fragments thereof by synthesis of the *pertussis* toxin or one or more subunits of the *pertussis* toxin.

The *pertussis* toxin or one or more subunits of the *pertussis* toxin so obtained are useful for the preparation of vaccines and diagnostic kits.

6 Claims, 23 Drawing Sheets

```
             1          10         20   25

S1    DDPPATVYRYDSRPPEDVFQNGFTAXG

S2    SQPGIVIPPQEQITGHGSPY

S3    VAPGIVIPPKALFTQGGGAYGXXXNG

S4    DVPYVLVKTNMVVTSVAMKPYEVTP
```

FIG. 2

```
          -40        -30        -20        -10       -1
     S2                  MPIDRKTLCHLLSVLPLALLGSHVARA
     S3                  MLINNKKLLHHILPILVLALLGMRTAQA
     S1              MRCTRAIRQTARTGWLTWLAILAVTAPVTSPAMA
     S4   MLRRFPTRTTAPGQGGARRSRVRALAWLLASGAMTHLSPALA
     S5              MQRQAGLPLKANPMHTIASILLSVLGIYSPADVA
```

FIG. 4

```
        10                  30                  50
GAATTCGTCGCCTCGCCCTGGTTCGCCGTCATGGCCCCCAAGGGAACCGACCCCAAGAT
 ⇢ORF A 70                  90                 110
AATCGTCCTGCTCAACCGCCACATCAACGAGGCGCTGCAGTCCAAGGCGGTCGTCGAGGC
       130                 150                 170
TTTGCCGCCCAAGGCGCCACGCCGGTCATCGCCACGCCGGATCAGACCCGCGGCTTCAT
       190                 210                 230
CGCAGACGAGATCCAGCGCTGGGCCGGCGTCGTGCGCGAAACCGGCGCCAAGCTGAAGTAG
       250                 270                 290
CAGCGCAGCCCTCCAACGCGCCATCCCCGTCCGGCCGGCACCATCCCGCATACGTGTTG
       310                 330                 350
GCAACCGCCAACGCGCATGCGTGCAGATTCGTCGTACAAAACCCTCGATTCTTCCGTACAT
       370                 390                 410
CCCGCTACTGCAATCCAACACGGCATGAACGCTCCTTCGGCGCAAAGTCGCGCGATGGT
       430                 450                 470
ACCGGTCACCGTCCGGACCGTGCTGACCCCCTGCCATGGTGTGATCCGTAAAATAGGCAC
       490         -35    510                 530  -10
CATCAAAACGCAGAGGGGAAGACGGGATGCGTTGCACTCGGGCAATTCGCCAAACCGCA
                                  MetArgCysThrArgAlaIleArgGlnThrAla
             550                 570
AGAACAGGCTGGCTGACGTGGCTGGCGATTCTTGCCGTCACGGCGCCCGTGACTTCGCCGG
ArgThrGlyTrpLeuThrTrpLeuAlaIleLeuAlaValThrAlaProValThrSerProA
       610                 630                 650
CATGGGCCGACGATCCTCCCGCCACCGTATACCGCTATGACTCCCGCCCGCCGGAGGAC
laTrpAlaAspAspProProAlaThrValTyrArgTyrAspSerArgProProGluAsp
   ↳S1
       670                 690                 710
GTTTTCCAGAACGGATTCACGGCGTGGGGAAACAACGACAATGTGCTCGACCATCTGACCG
ValPheGlnAsnGlyPheThrAlaTrpGlyAsnAsnAspAsnValLeuAspHisLeuThrG
                    750                 770
GACGTTCCTGCCAGGTCGGCAGCAGCAACAGCGCTTTCGTCTCCACCAGCAGCAGCCGG
lyArgSerCysGlnValGlySerSerAsnSerAlaPheValSerThrSerSerSerArg
       790                 810                 830
CGCTATACCGAGGTCTATCTCGAACATCGCATGCAGGAAGCGGTCGAGGCCGAACGCGCCG
ArgTyrThrGluValTyrLeuGluHisArgMetGlnGluAlaValGluAlaGluArgAlaG
       850                 870                 890
GCAGGGGCACCGGCCACTTCATCGGCTACATCTACGAAGTCCGCGCCGACAACAATTTC
lyArgGlyThrGlyHisPheIleGlyTyrIleTyrGluValArgAlaAspAsnAsnPhe
       910                 930                 950
TACGGCGCCGCCAGCTCGTACTTCGAATACGTCGACACTTATGGCGACAATGCCGGCCGTA
TyrGlyAlaAlaSerSerTyrPheGluTyrValAspThrTyrGlyAspAsnAlaGlyArgI
       970                 990                1010
TCCTCGCCGGCGCGCTGGCCACCTACCAGAGCGAATATCTGGCACACCGGCGCATTCCG
leLeuAlaGlyAlaLeuAlaThrTyrGlnSerGluTyrLeuAlaHisArgArgIlePro
      1030                1050                1070
CCCGAAAACATCCGCAGGGTAACGCGGGTCTATCACAACGGCATCACCGGCGAGACCACGA
ProGluAsnIleArgArgValThrArgValTyrHisAsnGlyIleThrGlyGluThrThrT
      1090                1110                1130
CCACGGAGTATTCCAACGCTCGCTACGTCAGCCAGCAGACTCGCGCCAATCCCAACCCC
hrThrGluTyrSerAsnAlaArgTyrValSerGlnGlnThrArgAlaAsnProAsnPro
      1150                1170                1190
TACACATCGCGAAGGTCCGTAGCGTCGATCGTCGGCACATTGGTGCGCATGGCGCCGGTGA
TyrThrSerArgArgSerValAlaSerIleValGlyThrLeuValArgMetAlaProVal
      1210                1230                1250
TAGGCGCTTGCATGGCGCGGCAGGCCGAAAGCTCCGAGGCCATGGCAGCCTGGTCCGAA
leGlyAlaCysMetAlaArgGlnAlaGluSerSerGluAlaMetAlaAlaTrpSerGlu
      1270                1290                1310
CGCGCCGGCGAGGCGATGGTTCTCGTGTACTACGAAAGCATCGCGTATTCGTTCTAGACCT
ArgAlaGlyGluAlaMetValLeuValTyrTyrGluSerIleAlaTyrSerPheEnd
```

FIG. 3A-1

```
                1330                    1350                    1370
       GGCCCAGCCCCGCCCAACTCCGGTAATTGAACAGCATGCCGATCGACCGCAAGACGCTC
                                         MetProIleAspArgLysThrLeu
              1390                    1410                    1430
       TGCCATCTCCTGTCCGTTCTGCCGTTGGCCCTCCTCGGATCTCACGTGGCGCGGGCCTCCA
       CysHisLeuLeuSerValLeuProLeuAlaLeuLeuGlySerHisValAlaArgAlaSerT
              1450                    1470                    1490           →S2
       CGCCAGGCATCGTCATTCCGCCGCAGGAACAGATTACCCAGCATGGCAGCCCCTATGGA
       hrProGlyIleValIleProProGlnGluGlnIleThrGlnHisGlySerProTyrGly
              1510                    1530                    1550
       CGCTGCGCGAACAAGACCCGTGCCCTGACCGTGGCGGAATTGCGCGGCAGCGGCGATCTGC
       ArgCysAlaAsnLysThrArgAlaLeuThrValAlaGluLeuArgGlySerGlyAspLeuG
              1570                    1590                    1610
       AGGAGTACCTGCGTCATGTGACGCGCGGCTGGTCAATATTTGCGCTCTACGATGGCACC
       lnGluTyrLeuArgHisValThrArgGlyTrpSerIlePheAlaLeuTyrAspGlyThr
              1630                    1650                    1670
       TATCTCGGCGGCGAATATGGCGGCGTGATCAAGGACGGAACACCCGGCGGCGCATTCGACC
       TyrLeuGlyGlyGluTyrGlyGlyValIleLysAspGlyThrProGlyGlyAlaPheAspL
              1690                    1710                    1730
       TGAAAACGACGTTCTGCATCATGACCACGCGCAATACGGGTCAACCCGCAACGGATCAC
       euLysThrThrPheCysIleMetThrThrArgAsnThrGlyGlnProAlaThrAspHis
              1750                    1770                    1790
       TACTACAGCAACGTCACCGCCACTCGCCTGCTCTCCAGCACCAACAGCAGGCTATGCGCGG
       TyrTyrSerAsnValThrAlaThrArgLeuLeuSerSerThrAsnSerArgLeuCysAlaV
              1810                    1830                    1850
       TCTTCGTCAGAAGCGGGCAACCGGTCATTGGCGCCTGCACCAGCCCGTATGACGGCAAG
       alPheValArgSerGlyGlnProValIleGlyAlaCysThrSerProTyrAspGlyLys
              1870                    1890                    1910
       TACTGGAGCATGTACAGCCGGCTGCGGAAAATGCTTTACCTGATCTACGTGGCCGGCATCT
       TyrTrpSerMetTyrSerArgLeuArgLysMetLeuTyrLeuIleTyrValAlaGlyIleS
              1930                    1950                    1970
       CCGTACGCGTCCATGTCAGCAAGGAAGAACAGTATTACGACTATGAGGACGCAACGTTC
       erValArgValHisValSerLysGluGluGlnTyrTyrAspTyrGluAspAlaThrPhe
              1990                    2010                    2030
       GAGACTTACGCCCTTACCGGCATCTCCATCTGCAATCCTGGATCATCCTTATGCTGAGACG
       GluThrTyrAlaLeuThrGlyIleSerIleCysAsnProGlySerSerLeuCysEnd
                                                       MetLeuArgAr
              2050                    2070                    2090
       CTTCCCCACTCGAACCACCGCCCCGGGACAGGGCGGCGCCCGGCGGTCGCGCGTGCGCG
       gPheProThrArgThrThrAlaProGlyGlnGlyGlyAlaArgArgSerArgValArgA
              2110                    2130                    2150
       CCCTGGCGTGGTTGCTGGCATCCGGCGCGATGACGCATCTTTCCCCCGCCCTGGCCGACGT
       laLeuAlaTrpLeuLeuAlaSerGlyAlaMetThrHisLeuSerProAlaLeuAlaAspVa
              2170                    2190                    2210           →S4
       TCCTTATGTGCTGGTGAAGACCAATATGGTGGTCACCAGCGTAGCCATGAAGCCGTATG
       lProTyrValLeuValLysThrAsnMetValValThrSerValAlaMetLysProTyrG
              2230                    2250                    2270
       AAGTCACCCCGACGCGCATGCTGGTCTGCGGCATCGCCGCCAAACTGGGCGCCGCGGCCAG
       luValThrProThrArgMetLeuValCysGlyIleAlaAlaLysLeuGlyAlaAlaAlaSe
              2290                    2310                    2330
       CAGCCCGGACGCGCACGTGCCGTTCTGCTTCGGCAAGGATCTCAAGCGTCCCGGCAGCA
       rSerProAspAlaHisValProPheCysPheGlyLysAspLeuLysArgProGlySerS
              2350                    2370                    2390
       GTCCCATGGAAGTCATGTTGCGCGCCGTCTTCATGCAACAACGGCCGCTGCGCATGTTTCT
       erProMetGluValMetLeuArgAlaValPheMetGlnGlnArgProLeuArgMetPheLe
```

FIG. 3A-2

```
                2410                2430                2450
     GGGTCCCAAGCAACTCACTTTCGAAGGCAAGCCCGCGCTCGAACTGATCCGGATGGTCG
                2470                2490                2510
     AATGCAGCGGCAAGCAGGATTGCCCCTGAAGGCGAACCCCATGCATACCATCGCATCCATC
      MetGlnArgGlnAlaGlyLeuProLeuLysAlaAsnProMetHisThrIleAlaSerIle
     uGlyProLysGlnLeuThrPheGluGlyLysProAlaLeuGluLeuIleArgMetValG
     luCysSerGlyLysGlnAspCysProEnd
                2530                2550                2570
     CTGTTGTCCGTGCTCGGCATATACAGCCCGGCTGACGTCGCCGGCTTGCCGACCCATCTG
      LeuLeuSerValLeuGlyIleTyrSerProAlaAspValAlaGlyLeuProThrHisLeu
                2590                2610       ↳S5 2630
     TACAAGAACTTCACTGTCCAGGAGCTGGCCTTGAAACTGAAGGGCAAGAATCAGGAGTTC
      TyrLysAsnPheThrValGlnGluLeuAlaLeuLysLeuLysGlyLysAsnGlnGluPhe
                2650                2670
     TGCCTGACCGCCTTCATGTCGGGCAGAAGCCTGGTCCGGGCGTGCCTGTCCGACGCGGGA
      CysLeuThrAlaPheMetSerGlyArgSerLeuValArgAlaCysLeuSerAspAlaGly
                2710                2730                2750
     CACGAGCACGACACGTGGTTCGACACCATGCTTGGCTTTGCCATATCCGCGTATGCGCTC
      HisGluHisAspThrTrpPheAspThrMetLeuGlyPheAlaIleSerAlaTyrAlaLeu
                2770                2790                2810
     AAGAGCCGGATCGCGCTGACGGTGGAAGACTCGCCGTATCCGGGCACTCCCGGCGATCTG
      LysSerArgIleAlaLeuThrValGluAspSerProTyrProGlyThrProGlyAspLeu
                2830                2850                2870
     CTCGAACTGCAGATCTGCCCGCTCAACGGATATTGCGAATGAACCCTTCCGGAGGTTTCG
      LeuGluLeuGlnIleCysProLeuAsnGlyTyrCysGluEnd
                2890                2910                2930
     ACGTTTCCGCGCAATCCGCTTGAGACGATCTTCCGCCCTGGTTCCATTCCGGGAACACCG
                2950                2970                2990
     CAACATGCTGATCAACAACAAGAAGCTGCTTCATCACATTCTGCCCATCCTGGTGCTCGC
        MetLeuIleAsnAsnLysLysLeuLeuHisHisIleLeuProIleLeuValLeuAl
                3010                3030                3050
     CCTGCTGGGCATGCGCACGGCCCAGGCCCTTGCGCCAGGCATCGTCATCCCGCCGAAGGC
      aLeuLeuGlyMetArgThrAlaGlnAlaValAlaProGlyIleValIleProProLysAl
                                              ↳S3
                3070                3090                3110
     ACTGTTCACCCAACAGGGCGGCGCCTATGGACGCTGCCCGAACGGAACCCGCGCCTTGAC
      aLeuPheThrGlnGlnGlyGlyAlaTyrGlyArgCysProAsnGlyThrArgAlaLeuTh
                3130                                  3170
     CGTGGCCGAACTGCGCGGCAACGCCGAATTGCAGACGTATTTGCGCCAGATAACGCCCGG
      rValAlaGluLeuArgGlyAsnAlaGluLeuGlnThrTyrLeuArgGlnIleThrProGl
                3190                3210                3230
     CTGGTCCATATACGGTCTCTATGACGGTACGTACCTGGGCCAGGCGTACGGCGGCATCAT
      yTrpSerIleTyrGlyLeuTyrAspGlyThrTyrLeuGlyGlnAlaTyrGlyGlyIleI
                3250                3270                3290
     CAAGGACGCGCCGCCAGGCGCGGGGTTCATTTATCGCGAAACTTTCTGCATCACGACCAT
      eLysAspAlaProProGlyAlaGlyPheIleTyrArgGluThrPheCysIleThrThrIl
                3310                3330                3350
     ATACAAGACCGGGCAACCGGCTGCGGATCACTACTACAGCAAGGTCACGGCCACGCGCCT
      eTyrLysThrGlyGlnProAlaAlaAspHisTyrTyrSerLysValThrAlaThrArgLe
                3370                3390                3410
     GCTCGCCAGCACCAACAGCAGGCTGTGCGCGGTATTCGTCAGGGACGGGCAATCGGTCAT
      uLeuAlaSerThrAsnSerArgLeuCysAlaValPheValArgAspGlyGlnSerValI
```

FIG. 3A-3

```
      3430              3450              3470
CGGAGCCTGCGCCAGCCCGTATGAAGGCAGGTACAGAGACATGTACGACGCGCTGCGGCG
eGlyAlaCysAlaSerProTyrGluGlyArgTyrArgAspMetTyrAspAlaLeuArgAr
      3490              3510              3530
CCTGCTGTACATGATCTATATGTCCGGCCTTGCCGTACGCGTCCACGTCAGCAAGGAAGA
gLeuLeuTyrMetIleTyrMetSerGlyLeuAlaValArgValHisValSerLysGluGl
      ─────────────────►◄─────────────────
      3550              3570              3590
GCAGTATTACGACTACGAGGACGCCACATTCCAGACCTATGCCCTCACCGGCATTTCCCT
uGlnTyrTyrAspTyrGluAspAlaThrPheGlnThrTyrAlaLeuThrGlyIleSerLe
                                              3650
CTGCAACCCGGCAGCGTCGATATGCTGAGCCGCCGGCTCGGATCTGTTCGCCTGTCCA‾T‾G‾
uCysAsnProAlaAlaSerIleCysEnd
      3670              3690              3710
‾T‾T‾T‾T‾T‾C‾C‾T‾T‾GACGGATACCGCGA|ATGAATCCCTTGAAAGACTTGAGAGCATCGCTACCGC
                              └─►ORF B
      3730              3750              3770
GCCTGGCCTTCATGGCAGCCTGCACCCTGTTGTCCGCCACGCTGCCCGACCTCGCCCAGG
      3790                                3830
CCGGCGGCGGGCTGCAGCGCGTCAACCACTTCATGGCGAGCATCGTGGTCGTACTGCGCG
      3850              3870              3890
GCGCGTCAGTGGCCACGGTGACCATCGCCATAATCTGGGCGGGCTACAAGCTGCTGTTCC
      3910              3930              3950
GGCACGCCGATGTGCTGGACGTGGTGCGAGTGGTGCTGGCGGGACTGCTGATCGGCGCAT
      3970              3990              4010
CGGCCGAAATCGCTCGTTATCTGCTGACCTGAATCCTGGACGTATCGAAC|ATGCGTGATC
                                              └─► ORF C
      4030              4050              4070
CGCTTTTCAAGGGCTGCACCCGGCCCGCGATGCTGATGGGCGTACCCGCCACGCCGCTGG
      4090              4110
CCGTGTGCAGCGGCACCATTGCCCTGCTGGGCATCTGGTTCAGCATCGCCTTTCTGGCCT
      4150              4170              4190
TGTTTCCCGTGGCATTGCTGGCGATGCGGATCATGATCCGGCGCGATGACCAGCAGTTCC
      4210              4230              4250
GCCTGATCTGGCTTTACCTGCGCATGCGTTGGCTGAGCCGGGACCGCACGCATGCGTTCT
      4270              4290              4310
GGCAAAGTACCGTCTATGCGCCGCTGCGTTACGCCGAGCGCCgccGGCGCCTGCGcAAGC
      4330              4350              4370
C|ATGAACCGGCGCGGCGGCCAGACCGCATTTGCGGCCATTGCGCGCAACGAGCGCGCCAT
└─►ORF D
      4390              4410              4430
CGCTGCGTTCATCCCCTACAGCAGCCACCTGACGGACACGACGCTGATCACCCATGGCGC
                  4470              4490
GGACCTGGTCCGCACCTGGCGCGTACAGGGGATCGCCTTCGAAAGCGCCGAGCCAGAGCT
      4510              4530              4550
GGTTTCGCAGCGCCATGAACAGCTCAACGGCCTGTGGCGCGCCATCTCGTGCGAGCAGGT
      4570              4590              4610
CGCGCTTTGGATCCATTGCATCCGGCGCAAGACGCAGGCCGGGTTGGATGCGCGGTACGA
      4630              4650              4670
AAATCCGTTCTGCCGCGCGCTCGACGCCTCGTACAACGCCCGGCTGAACGCGCGGCAGGC
      4690
AATGACGAACGAATTC
```

FIG. 3A-4

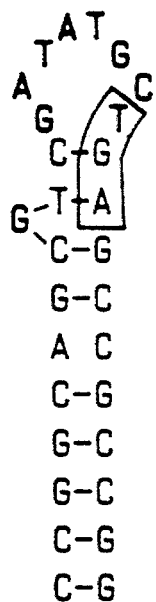

..TCTGCAAC CTCGGATCTGTTCGCCTGTCCA<u>TGTTTTTCCTTG</u>AC....

FIG. 5B

```
            -20           -10            ↓
S2    MPI.DRKTLCHLLSVLPLALLGSHVARA STPGIVIPPQEGITQHGSPYGR    22
      | |  | | | |  | ||||| | |  ||||||||    || |  |||
S3    MLINNKKLLHHILPILVLALLGMRTAGA VAPGIVIPPKALFTQGGGAYGR    22
                                 ↑

S2    CANKTRALTVAELRGSGDLQEYLRHVTRGWSIFALYDGTYLGGEYGGVIK    72
      | | |||||||||||  ||  ||| | || ||  ||||||||  ||| ||
S3    CPNGTRALTVAELRGNAELQTYLRQITPGWSIYGLYDGTYLGQAYGGIIK    72

S2    DGTPGGAFDLKTTFCIMTTRNTGQPATDHYYSNVTATRLLSSTNSRLCAV    122
      |  || |    ||||  |    |||||  ||||| |||||| ||||||||
S3    DAPPGAGFIYRETFCITTIYKTGQPAADHYYSKVTATRLLASTNSRLCAV    122

S2    FVRSGQPVIGACTSPYDGKYWSMYSRLRKMLYLIYVAGISVRVHVSKEEQ    172
      ||| || ||||| ||||  |||  | || || || || |  |||||||||
S3    FVRDGQSVIGACASPYEGRYRDMYDALRRLLYMIYMSGLAVRVHVSKEEQ    172

S2    YYDYEDATFETYALTGISICNPGSSLC    199
      |||||||||  ||||||||| ||| | |
S3    YYDYEDATFQTYALTGISLCNPAASIC    199
```

FIG. 6

```
        1       10        20                           30       40        50
PT-S1    DDPPATVYRYDSRPPEDVFQNGFTAWGN...........NDNVLDHLTGRSCQVGSSNSAFVSTSSSRR
CT-A    NDDKL...YRADSRPPDEIKQSGGLMPRGQSEYFDRGTQMNINLYDHARGTQTGFVRHDDGYVSTSISLR
        1          10        20        30        40        50        60

60        70        80        90         100
PT-S1   YTEVVYLEHRMQEAVEAERAGRGTGHFIGYIYEVRAD..NNFYGA
CT-A    SAHLVGQTILS.............GHSTYYIY.VIATAPNMFNVN
         70                     80         90     98
```

PTE211 (S2)

Fragment Sau96-Sma1 (1433-2064) cloned blunt in PEX31a/BamH1-blunt

```
      EcoR1          (BamH1-Sau96)
      _____         _____
....gga att cgg gcg acc gga tcG GCC TCC ACG CCA......
....gly ile arg ala thr gly ser ALA SER THR PRO......
                                 ---
```

PTE221 (S3)

Fragment SpH1-Dde1 (3014-3628) cloned blunt in PEX34c/BamH1-blunt

```
      EcoR1          (BamH1-Sph1)
      _____         _____
....gg aat tcg cgc gac cgg atc CGC ACG GCC CAG GCC GTT GCA CCA....
...... asn ser arg asp arg ile ARG THR ALA GLN ALA VAL ALA PRO....
                                _____
```

PTE240 (S4)

Fragment BstN1-BstN1 (2151-2600) cloned blunt in PEX31b/BamH1-blunt

```
      EcoR1          (BamH1-BstN1)
      _____         _____
....g gaa ttc gcg cga ccg gat cTG GCC GAC GTT CCT....
......glu phe ala arg pro asp LEU ALA ASP VAL PRO....
                               _____
```

PTE230 (S5)

Fragment Aat2-SnaB1 (2558-3210) cloned blunt in PEX31a/BamH1-blunt

```
      EcoR1          (BamH1-Aat2)
      _____         _____
...g gga att cgc gcg acc gga tcC GCC GGC TTG CCG....
.....gly ile arg ala thr gly SER ALA GLY LEU PRO....
                              _____
```

FIG. 9

```
   1  GAATTCGTCG CCTCGCCCTG GTTCGCCGTC ATGGCCCCCA AGGGAACCGA
  51  CCCCAAGATA ATCGTCCTGC TCAACCGCCA CATCAACGAG GCGCTGCAGT
 101  CCAAGGCGGT CGTCGAGGCC TTTGCCGCCC AAGGCGCCAC GCCGGTCATC
 151  GCCACGCCGG ATCAGACCCG CGGCTTCATC GCAGACGAGA TCCAGCGCTG
 201  GGCCGGCGTC GTGCGCGAAA CCGGCGCCAA GCTGAAGTAG CAGCGCAGCC
 251  CTCCAACGCG CCATCCCCGT CCGGCCGGCA CCATCCCGCA TACGTGTTGG
 301  CAACCGCCAA CGCGCATGCG TGCAGATTCG TCGTACAAAG CCCTCGATTC
 351  TTCCGTACAT CCCGCTACTG CAATCCAACA CGGCATGAAC GCTCCTTCGG
 401  CGCAAAGTCG CGCGATGGTA CCGGTCACCG TCCGGACCGT GGTGACCCCC
 451  CTGCCATGGT GTGATCCGTA AAATAGGCAC CATCAAAACG CAGAGGGGAA
 501  GACGGGATGC GTTGCACTCG GCAATTCGC  CAAACCGCAA GAACAGGCTG
 551  GCTGACGTGG CTGGCGATTC TTGCCGTCAC GGCGCCCGTG ACTTCGCCGG
 601  CATGGGCCGA CGATCCTCCC GCCACCGTAT ACCGCTATGA CTCCCGCCCG
 651  CCGGAGGACG TTTTCCAGAA CGGATTCACG GCGTGGGGAA ACAACGACAA
 701  TGTGCTCGAC CATCTGACCG GACGTTCCTG CCAGGTCGGC AGCAGCAACA
 751  GCGCTTTCGT CTCCACCAGC AGCAGCCGGC GCTATACCGA GGTCTATCTC
 801  GAACATCGCA TGCAGGAAGC GGTCGAGGCC GAACGCGCCG GCAGGGGCAC
 851  CGGCCACTTC ATCGGCTACA TCTACGAAGT CCGCGCCGAC AACAATTTCT
 901  ACGGCGCCGC CAGCTCGTAC TTCGAATACG TCGACACTTA TGGCGACAAT
 951  GCCGGCCGTA TCCTCGCCGG CGCGCTGGCC ACCTACCAGA GCGAATATCT
1001  GGCACACCGG CGCATTCCGC CGAAAACAT  CCGCAGGGTA ACGCGGGTCT
1051  ATCACAACGG CATCACCGGC GAGACCACGA CCACGGAGTA TTCCAACGCT
```

FIG. 13A

```
1101  CGCTACGTCA GCCAGCAGAC TCGCGCCAAT CCCAACCCCT ACACATCGCG
                                                A          T
1151  AAGGTCCGTA GCGTCGATCG TCGGCACATT GGTGCGCATG GCGCCGGTGA
                ACC
      [CG]                                   [C]
1201  [TA]GGCGCTTG CATGGCGCGG CAGGCCGAAA GG[T]CCGAGGC CATGGCAGCC
      [CG]                                   [C]
1251  TGGTCCGAAC GCGCCGGCGA GGCGATGGTT CTCGTGTACT ACGAAAGCAT
             G        A
1301  CGCGTATTCG TTCTAGACCT GGCCCAGCCC CGCCCAACTC CGGTAATTCA
                                                          C
1351  ACAGCATGCC GATCGACCGC AAGACGCTCT GCCATCTCCT GTCCGTTCTG
                    AG
                 →S2
1401  CCGTTGGCCC TCCTCGGATC TCACGTGGCG CGGGCCTCCA CGCCAGGCAT
              T         G          C
                                          [C]  [G]
1451  CGTCATTCCG CCGCAGGAAC AGATTACCCA GCA[T]GGC[A]GC CCCTATGGAC
                                          [C]  [G]
1501  GCTGCGCGAA CAAGACCCGT GCCCTGACCG TGGCGGAATT GCGCGGCAGC
1551  GGCGATCTGC AGGAGTACCT GCGTCATGTG ACGCGCGGCT GGTCAATATT
1601  TGCGCTCTAC GATGGCACCT ATCTCGGCGG CGAATATGGC GGCGTGATCA
1651  AGGACGGAAC ACCCGGCGGC GCATTCGACC TGAAAACGAC GTTCTGCATC
                                                        G          T
1701  ATGACCACGC GCAATACGGG TCAACCCGCA ACGGATCACT ACTACAGCAA
                       C
1751  CGTCACCGCC ACTCGCCTGC TCTCCAGCAC CAACAGCAGG CTATGCGCGG
1801  TCTTCGTCAG AAGCGGGCAA CCGGTCATTG GCGCCTGCAC CAGCCCGTAT
1851  GACGGCAAGT ACTGGAGCAT GTACAGCCGG CTGCGGAAAA TGCTTTACCT
                       A
1901  GATCTACGTG GCCGGCATCT CCGTACGCGT CCATGTCAGC AAGGAAGAAC
                 C   A
1951  AGTATTACGA CTATGAGGAC GCAACGTTCG AGACTTACGC CCTTACCGGC
                             G                                      T
2001  ATCTCCATCT GCAATCCTGG ATCATCCTTA TGCTGAGACG CTTCCCCACT
                                    →S4
                                      C   C
2051  CGAACCACCG CCCCGGGACA GGGCGGCGCC CGGCGGTCGC GCGTGCGCGC
                                        A      T          CA
2101  CCTGGCGTGG TTGCTGGCAT CCGGCGCGAT GACGCATCTT TCCCCCGCCC
      A             G
2151  TGGCCGACGT TCCTTATGTG CTGGTGAAGA CCAATATGGT GGTCACCAGC
```

FIG. 13B

```
                                                    G
2201  GTAGCCATGA AGCCGTATGA AGTCACCCCG ACGCGCATGC TGGTCTGCGG

G
2251  CATCGCCGCC AAACTGGGCG CCGCGGCCAG CAGCCCGGAC GCGCACGTGC
                    G

T                             CT                            C
2301  CGTTCTGCTT CGGCAAGGAT CTCAAGCGTC CCGGCAGCAG TCCCATGGAA

C
2351  GTCATGTTGC GCGCCGTCTT CATGCAACAA CGGCCGCTGC GCATGTTCT
                                                        C

2401  GGGTCCCAAG CAACTCACTT TCGAAGGCAA GCCCGCGCTC GAACTGATCC

G
2451  GGATGGTCGA ATGCAGCGGC AAGCAGGATT GCCCCTGAAG GCGAACCCCA
                 └→S5

2501  TGCATACCAT CGCATCCATC CTGTTGTCCG TGCTCGGCAT ATACAGCCCG

C         C                              G
2551  GCTGACGTCG CCGGCTTGCC GACCCATCTG TACAAGAACT TCACTGTCCA
       C

AA              A                C
2601  GGAGCTGGCC TTGAAACTGA AGGGCAAGAA TCAGGAGTTC TGCCTGACCG

C  A                                     A
2651  CCTTCATGTC GGGCAGAAGC CTGGTCCGGG CGTGCCTGTC CGACGCGGGA
             C

G AC  G    G
2701  CACGAGCACG ACACGTGGTT CGACACCATG CTTGGCTTTG CCATATCCGC

A
2751  GTATGCGCTC AAGAGCCGGA TCGCGCTGAC GGTGGAAGAC TCGCCGTATC

2801  CGGGCACTCC CGGCGATCTG CTCGAACTGC AGATCTGCCC GCTCAACGGA

C      C C      A  T G      C
2851  TATTGCGAAT GAACCCTTCC GGAGGTTTCG ACGTTTCCGC GCAATCCGCT
                      T

T
2901  TGAGACGATC TTCCGCCCTG GTTCCATTCC GGGAACACCG CAACATGCTG

C              C
2951  ATCAACAACA GAAGCTGCT TCATCACATT CTGCCCATCC TGGTGCTCGC
                                              └→S3

G          A
3001  CCTGCTGGGC ATGCGCACGG CCCAGGCCGT TGCGCCAGGC ATCGTCATCC

C  C        A
3051  CGCCGAAGGC ACTGTTCACC CAACAGGGCG CGCCTATGG ACGCTGCCCG

C    G      CG
3101  AACGGAACCC GCGCCTTGAC CGTGGCCCAA CTGCGCGGCA ACGCCGAATT

A                                        G
3151  GCAGACGTAT TTGCGCCAGA TAACGCCCGG CTGGTCCATA TACGGTCTCT
```

FIG. 13C

```
                               T
3201  ATGACGGTAC GTACCTGGGC CAGGCGTACG GCGGCATCAT CAAGGACGCG
         GC  G C    GC CTC           AGA       C
3251  CCGCCAGGCG CGGGGTTCAT TTATCGCGAA ACTTTCTGCA TCACGACCAT
       C  T C        A  G     A A A
3301  ATACAAGACC GGGCAACCGG CTGCGGATCA CTACTACAGC AAGGTCACGG
      G
                       G              G              C      C
3351  CCACGCGCCT GCTCGCCAGC ACCAACAGCA GGCTGTGCGC GGTATTCGTC
         T AA     C  C      C         A  C         C  A TC
3401  AGGGACGGGC AATCGGTCAT CGGAGCCTGC GCCAGCCCGT ATGAAGGCAG
                                 C
           G                       T               T          G
3451  GTACAGAGAC ATGTACGACG CGCTGCGGCG CCTGCTGTAC ATGATCTATA
                                T
                                I
           T                                     A
3501  TGTCCGGCCT TGCCGTACGC GTCCACGTCA GCAAGGAAGA GCAGTATTAC
          T  A       G       G                    T C  A
3551  GACTACGAGG ACGCCACATT CCAGACCTAT GCCCTCACCG GCATTTCCCT
      ──────────────→      ←──────────
              G  A  C         T    TC  C    C T
3601  CTGCAACCCG GCAGCGTCGA TATGCTGAGC CGCCGGCTCG GATCTGTTCG
        ACC G CA     CCA  C     A     TC  A       C    G
3651  CCTGTCCATG TTTTTCCTTG ACGGATACCG CGAATGAATC CCTTGAAAGA
           C
         G  A G  C A GG                               T
3701  CTTGAGAGCA TCGCTACCGC GCCTGGCCTT CATGGCAGCC TGCACCCTGT
      C
        CTG              T          GA         C    A
3751  TGTCCGCCAC GCTGCCCGAC CTCGCCCAGG CCGGCGGCGG GCTGCAGCGC
         AG              G    CAC      G          A  G
3801  GTCAACCACT TCATGGCGAG CATCGTGGTC GTACTGCGCG GCGCGTCAGT
             C              C  A        C
3851  GGCCACGGTG ACCATCGCCA TAATCTGGGC GGGCTACAAG CTGCTGTTCC
3901  GGCACGCCGA TGTGCTGGAC GTGGTGCGAG TGGTGCTGGC GGGACTGCTG
                                      C
3951  ATCGGCGCAT CGGCCGAAAT CGCTCGTTAT CTGCTGACCT GAATCCTGGA
                            C                          T
4001  CGTATCGAAC ATGCGTGATC CGCTTTTCAA GGGCTGCACC CGGCCCGCGA
4051  TGCTGATGGG CGTACCCGCC ACGCCGCTGG CCGTGTGCAG CGGCACCATT
4101  GCCCTGCTGG GCATCTGGTT CAGCATCGCC TTTCTGGCCT TGTTTCCCGT
4151  GGCATTGCTG GCGATGCGGA TCATGATCCG GCGCGATGAC CAGCAGTTCC
```

FIG. 13D

```
4201  GCCTGATCTG GCTTTACCTG CGCATGCGTT GGCTGAGCCG GGACCGCACG
4251  CATGCGTTCT GGCAAAGTAC CGTCTATGCG CCGCTGCGTT ACGCCGAGCG
4301  CCGCCGGCGC CTGCGCAAGC CATGAACCGG CGCGGCGGCC AGACCGCATT
                                     C
4351  TGCGGCCATT GCGCGCAACG AGCGCGCCAT CGCTGCGTTC ATCCCCTACA
4401  GCAGCCACCT GACGGACACG ACGCTGATCA CCCATGGCGC GGACCTGGTC
4451  CGCACCTGGC GCGTACAGGG GATCGCCTTC GAAAGCGCCG AGCCAGAGCT
4501  GGTTTCGCAG CGCCATGAAC AGCTCAACGG CCTGTGGCGC GCCATCTCGT
4551  GCGAGCAGGT CGCGCTTTGG ATCCATTGCA TCCGGCGCAA GACGCAGGCC
                A
4601  GGGTTGGATG CGCGGTACGA AAATCCGTTC TGCCGCGCGC TCGACGCCTC
                                                          G
4651  GTACAAGGCC CGGCTGAACG CGCGGCAGGC AATGACGAAC GAATTCTACC
                                                          G
4701  TCACCCTGGT ATATCGGCCT GGCCACGCCG CGCTCGGCAA GCGTGCGCAT
4751  CACGGCCAGG CCGAGGTCCG CCGGCAACTG CTGGCCCATG TACGACGCAT
                                                          G
4801  GGACGAAATC GGATCCCTGA TCGAAACGAC GCTGCGCAGC CATGGCGAGA
4851  ACCACGAGCA GGCCATCACC GTGCTGGGCT GCGAGACGGA CAGCGCCGGC
4901  CGGCGATACT CCCGGACGCT GACCCTGCTC GAATTC
```

FIG. 13E

S1
```
  1  MRCTRAIRQT  ARTGWLTWLA  ILAVTAPVTS  PAW ADDPPAT  VYRYDSRPPE
                 R                          ↓
                         E
 51  DVFQNGFTAW  GNNDNVLDHL  TGRSCQVGSS  NSAFVSTSSS  RRYTEVYLEH
                         E
101  RMQEAVEAER  AGRGTGHFIG  YIYEVRADNN  FYGAASSYFE  YVDTYGDNAG
                                     I
                                                              P
151  RILAGALATY  QSEYLAHRRI  PPENIRRVTR  VYHNGITGET  TTTEYSNARY
                                     T                        P L
                                                T        P
201  VSQQTRANPN  PYTSRRSVAS  IVGTLVRMAP  VIGACMARQA  ESSEAMAAWS
              T           T                     T        P
251  ERAGEAMVLV  YYESIAYSF*
              T
```

S2
```
                                          ↓              G
  1  MPIDRKTLCH  LLSVLPLALL  GSHVARASTP  GIVIPPQEQI  TQHGSPYGRC
              S                  F   C                        G
 51  ANKTRALTVA  ELRGSGDLQE  YLRHVTRGWS  IFALYDGTYL  GGEYGGVIKD
                                      R    F
101  GTPGGAFDLK  TTFCIMTTRN  TGQPATDHYY  SNVTATRLLS  STNSRLCAVF
151  VRSGQPVIGA  CTSPYDGKYW  SMYSRLRKML  YLIYVAGISV  RVHVSKEEQY
                          *
201  YDYEDATFET  YALTGISICN  PGSSLC*
```

FIG. 15A

```
S3
                      L           R↓        S           L K
  1   MLINNKKLLH  HILPILVLAL  LGMRTAQAVA  PGIVIPPKAL  FTQQGGAYGR

A           T                                    S
 51   CPNGTRALTV  AELRGNAELQ  TYLRQITPGW  SIYGLYDGTY  LGQAYGGIIK

R AGAL      QKP         Y DT                      G
101   DAPPGAGFIY  RETFCITTIY  KTGQPAADHY  YSKVTATRLL  ASTNSRLCAV
                         M
          A   KPL      TR QSS     G    V              V
151   FVRDGQSVIG  ACASPYEGRY  RDMYDALRRL  LYMIYMSGLA  VRVHVSKEEQ
                                 V
              E           I
201   YYDYEDATFQ  TYALTGISLC  NPAASIC*

S4           L                       P              T M H  Q↓
  1   MLRRFPTRTT  APGQGGARRS  RVRALAWLLA  SGAMTHLSPA  LADVPYVLVK

51   TNMVVTSVAM  KPYEVTPTRM  LVCGIAAKLG  AAASSPDAHV  PFCFGKDLKR

S
101   PGSSPMEVML  RAVFMQQRPL  RMFLGPKQLT  FEGKPALELI  RMVECSGKQD

151   CP*

S5    V                         ↓                                    T
  1   MQRQAGLPLK  ANPMHTIASI  LLSVLGIYSP  ADVAGLPTHL  YKNFTVQELA

D   L        P                E  RTRG
 51   LKLKGKNQEF  CLTAFMSGRS  LVRACLSDAG  HEHDTWFDTM  LGFAISAYAL
                         P
101   KSRIALTVED  SPYPGTPGDL  LELQICPLNG  YCE*
```

FIG. 15B

PERTUSSIS TOXIN AND USE IN VACCINES

This is a division of application Ser. No. 07/968,162, filed Oct. 29, 1992, now abandoned, which is a continuation of Ser. No. 07/634,100, filed Dec. 26, 1990, now abandoned, which is a continuation of Ser. No. 07/006,438 filed Jan. 23, 1987, now abandoned.

The present invention relates to a cloned and sequenced Eco RI fragment of *Bordetella pertussis* chromosomal DNA containing the genes which code for the five subunits of the *pertussis* toxin, useful for the preparation of the *pertussis* toxin or of one or more subunits of the *pertussis* toxin.

The present invention also relates to a hybrid plasmid containing the cloned and sequenced DNA fragment or further fragments thereof and to a micro-organism transformed by the hybrid plasmid and capable of expressing the cloned DNA fragment or further fragments thereof by synthesis of the *pertussis* toxin or one or more subunits of the *pertussis* toxin.

The invention also concerns a method for the preparation of the *pertussis* toxin or one or more subunits of the *pertussis* toxin which includes the growth of the micro-organism transformed by the hybrid plasmid in a suitable culture medium.

The *pertussis* toxin or one or more subunits of the *pertussis* toxin thus obtained is useful for the preparation of vaccines and diagnostic kits.

*Pertussis* is an infection of the respiratory tract caused by *Bordetella pertussis* (*B. pertussis*), a Gram-negative coccobacillus which is transmitted directly through the air during a catarrhal or convulsive period from the infirmed to a susceptible healthy individual.

*Pertussis* may cause respiratory complications, nerve damage and high mortality, particularly in children in low socio-economic groups and in new born babies without material, anti-*pertussis* antibodies. The clinical course of *pertussis* includes four phases: incubation, cattarhal phase, paroxysmic phase, and a convalescent phase.

During the first two phases there are symptoms comparable to those of a common cold and the *B. pertussis* may be isolated easily from the patients.

During the paroxysmic phase, characterised by the symptoms of *pertussis* itself, the bacterium is isolated only in 50% of cases.

During the convalescent phase it is no longer possible to isolate *B. pertussis* from the nasopharynx although the patients still have symptoms of *pertussis*.

It is clear from this that the more violent clinical indications of the illness occur after the disappearance of the bacteria and from this it may be inferred that *pertussis* is not due to invasion of the respiratory tract by the bacteria but to a toxic state induced by the bacteria but which remains even after their disappearance.

The change of *B. pertussis* from phase I (virulent) to phase III (non-virulent) is accompanied by a loss of capacity to synthesize certain substances such as: the *pertussis* toxin (PT), haemolysin (hly), adenylcyclase (Adc) and the dermonecrotic toxic (Dmt).

Tests carried out by Munoz, J. J. et al. (1981) (Inf. Immun. 32. 243) have shown that a vaccine constituted by the *pertussis* toxin alone, suitably detoxified with glutaraldehyde, is capable of protecting mice from death due to the intracerebral administration of bacteria in phase I.

Recent studies (Weiss, A. A. et al. (1983) Inf. Immun. 42, 33; Weiss, A. A. et al (1984) J. Inf. Dis. 150, 219) have shown that not all these five substance contribute with equal effect to the virulence of *B. pertussis*. Weiss has succeeded in isolating the mutants which have lost selectively only one of the factors of the virulence by the insertion of a transposable element, a transposon (TN5), into the genome of *B. pertussis*, from tests carried out in animals, it was found that only the mutants which had lost their capacity to synthesize PT or Adc had, at the same time, lost their virulence.

Hence, the *pertussis* toxin (PT) is the major factor in the virulence of *Bordetella pertussis*.

The *pertussis* toxin, a protein with a molecular weight of about 100,000 daltons, is produced and released into the extra cellular environment by *Bordetella pertussis* during phase I.

PT has an enzymatic activity and deactivates ADP-ribosilandol, a GTP-dependent protein which is involved in the deactivation of cellular adenylcyclase.

Like other toxins, the *pertussis* toxin is also constituted by two different fragments: A and B.

The A fragment, which is toxic, comprises a single polypeptide S1 (subunit S1) having a molecular weight of about 28,000 daltons, which can bind an ADP-ribose group to a GTP-binding protein $G_i$, which inhibits adenylate cyclase, involved in the transmission of signals from the outside to the inside of cells.

The B fragment comprises five polypeptides, S2, S3, S4 and S5 (subunits S2, S3, S4, S5) with molecular weights of 23,000, 22,000, 12,000 and 9,000 daltons respectively, disposed as two dimers S2+S4 and S3+S4 and a monomer S5.

The B fragment binds to membrane receptors of eucaryotic cells facilitating entry of S1 into the cells.

At present a *pertussis* vaccine is used which, although giving permanent immunity, has numerous disadvantages.

The vaccine is in fact constituted by virulent bacteria (phase I) treated at 56° C. for 30 minutes to remove a toxin which is heat-labile (dermonecrotic toxin) and killed by merthiolate.

Since the bacteria are not subjected to any detoxification treatment, any toxic substance which withstands 56° C. for 30 minutes is included in the vaccine.

The presence of such toxic substances, particularly from the PT, causes side effects which vary from simple flushing to permanent neurological damage and/or death.

All this has meant that over the last ten years the use of the vaccine has been reduced drastically with a consequence re-explosion of cases of *pertussis*.

Recently a vaccine has been prepared which is constituted essentially by fibrous haemagglutinin (FHA) and *pertussis* toxin detoxified with formaldehyde (Sato Y., et al: Lancet Jan. 21. 122 (1984)).

However this vaccine has disadvantages such as: the presence of side effects, even through less than those of the conventional vaccine; obtaining a product which is too crude to be used as such; and extreme variability of the product from preparation to preparation.

There is thus a need to provide an effective vaccine which can be produced on a large scale and which does not have the disadvantages noted above.

Thus, for example, recent developments in the biochemical field and in the field of genetic engineering have made it possible to prepare synthetic vaccines and micro-organisms capable of producing proteins useful for the preparation of vaccines with high yields.

In every case a key element for the preparation of the vaccines is a knowledge of the amino acid sequence of the protein and the nucleotide sequence of the gene and/or genes which code for the protein.

Once the gene which codes for a certain protein has been cloned and its nucleotide and amino acid sequences have been determined, the production of these on a large scale and the construction of synthetic vaccines is possible with current techniques.

At present nothing is known of the nature, structure and expression of the gene and/or genes of the *pertussis* toxin and no data other than the amino acid composition of the individual subunits of the *pertussis* toxin is available.

Accordingly, by the present invention there has been determined the aminoterminal amino acid sequence of the subunits S1, S2, S3 and S4 of the *pertussis* toxin and an Eco RI-fragment of *Bordetella pertussus* chromosomal DNA has been cloned and sequenced, the fragment having 4696 base pairs and containing the genes which code for the five subunits of the *pertussis* toxin, useful for the preparation of the *pertussis* toxin or of one or more subunits of the *pertussis* toxin. Thus a subject of the present invention is a cloned and sequenced 4696-base-pair Eco RI fragment of *Bordetella pertussis* chromosomal DNA containing the genes which code for the five subunits of the *pertussis* toxin or fragments thereof, useful for the production of the *pertussis* toxin or of one or more subunits of the *pertussis* toxin.

Another subject of the invention is a hybrid plasmid containing the cloned and sequenced DNA fragment or further fragments thereof.

A further subject of the present invention is a micro-organism transformed by the hybrid plasmid and capable of expressing the cloned DNA fragment or its further fragments by synthesis of the *pertussis* toxin or of one or more subunits of the *pertussis* toxin.

Another subject of the present invention is a method for the preparation of the *pertussis* toxin or of one or more subunits of the *pertussis* toxin by growth of the transformed micro-organism.

A further subject of the present invention is the use of the *pertussus* toxin or of one or more subunits of the pertussis toxin for the preparation of anti-*pertussis* vaccines and diagnostic kits.

Figure 3B:
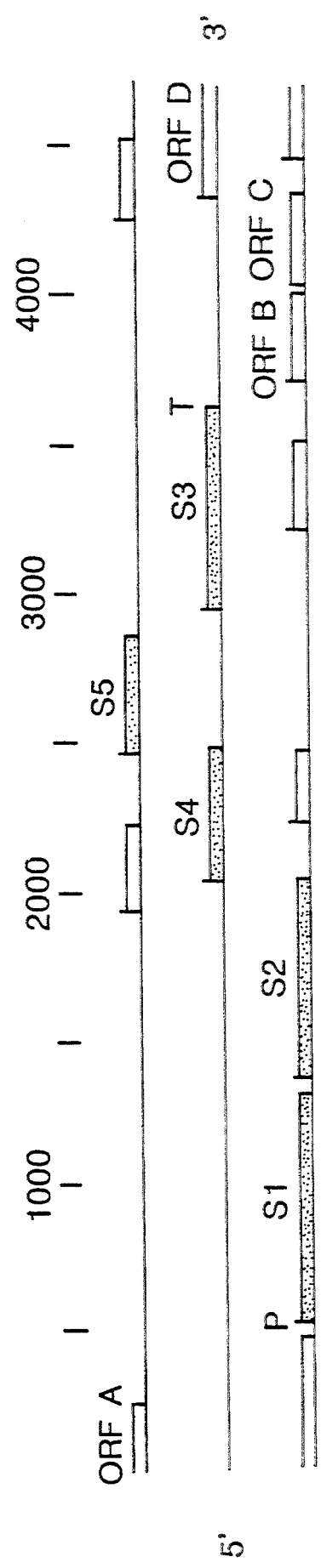
Figure 5A:
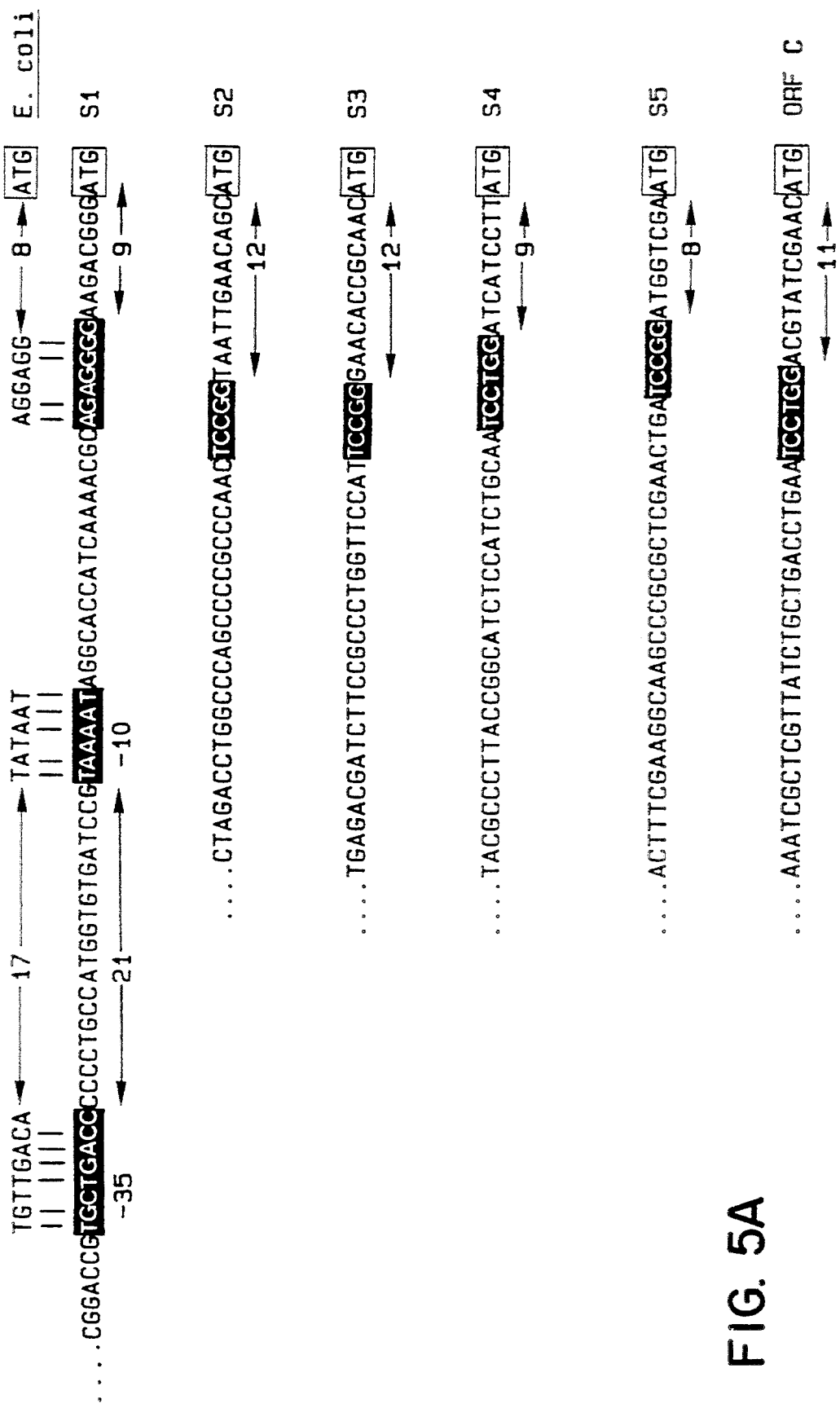
Figure 8:
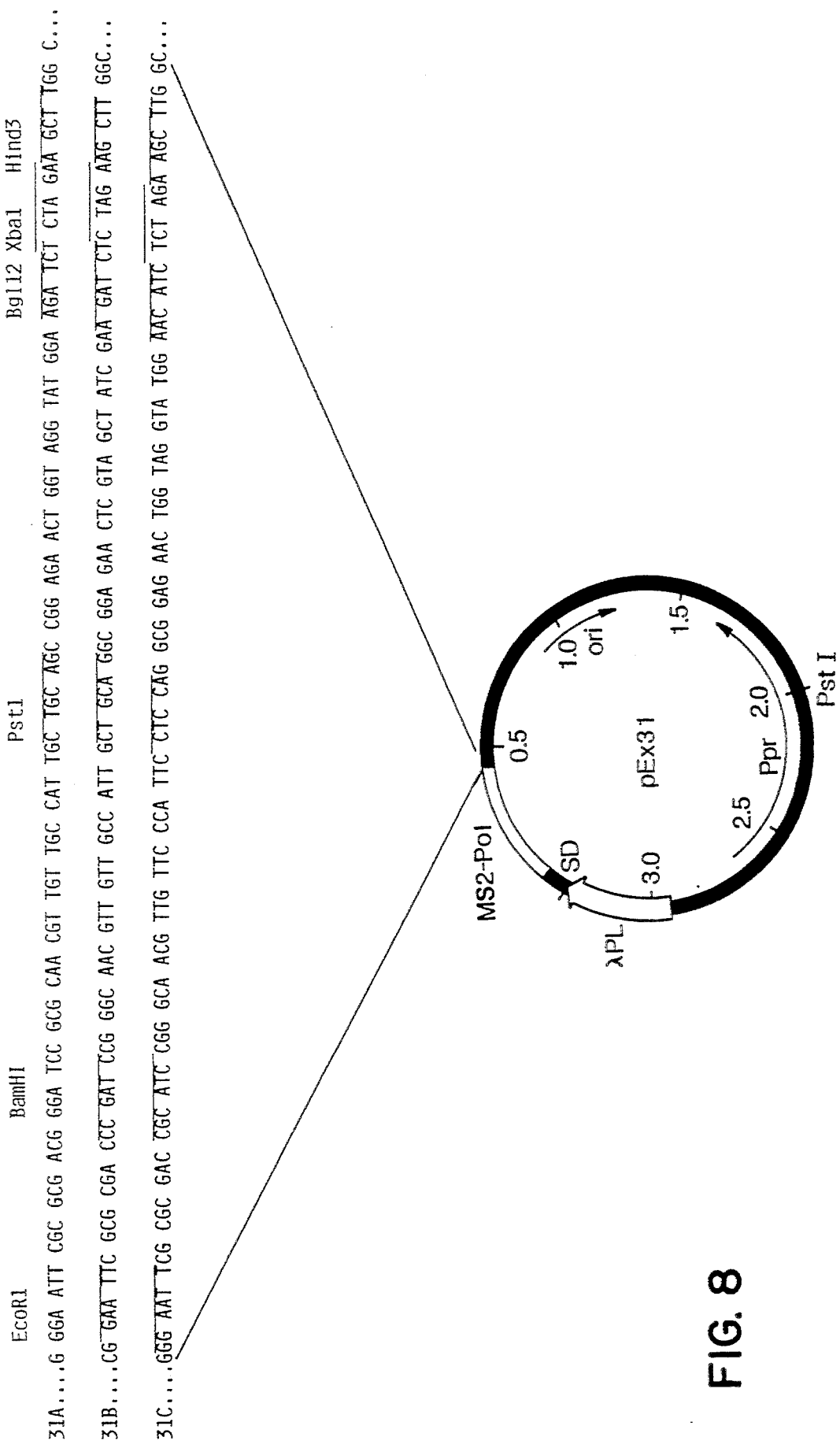
Figures 10A, 10B, 10C:
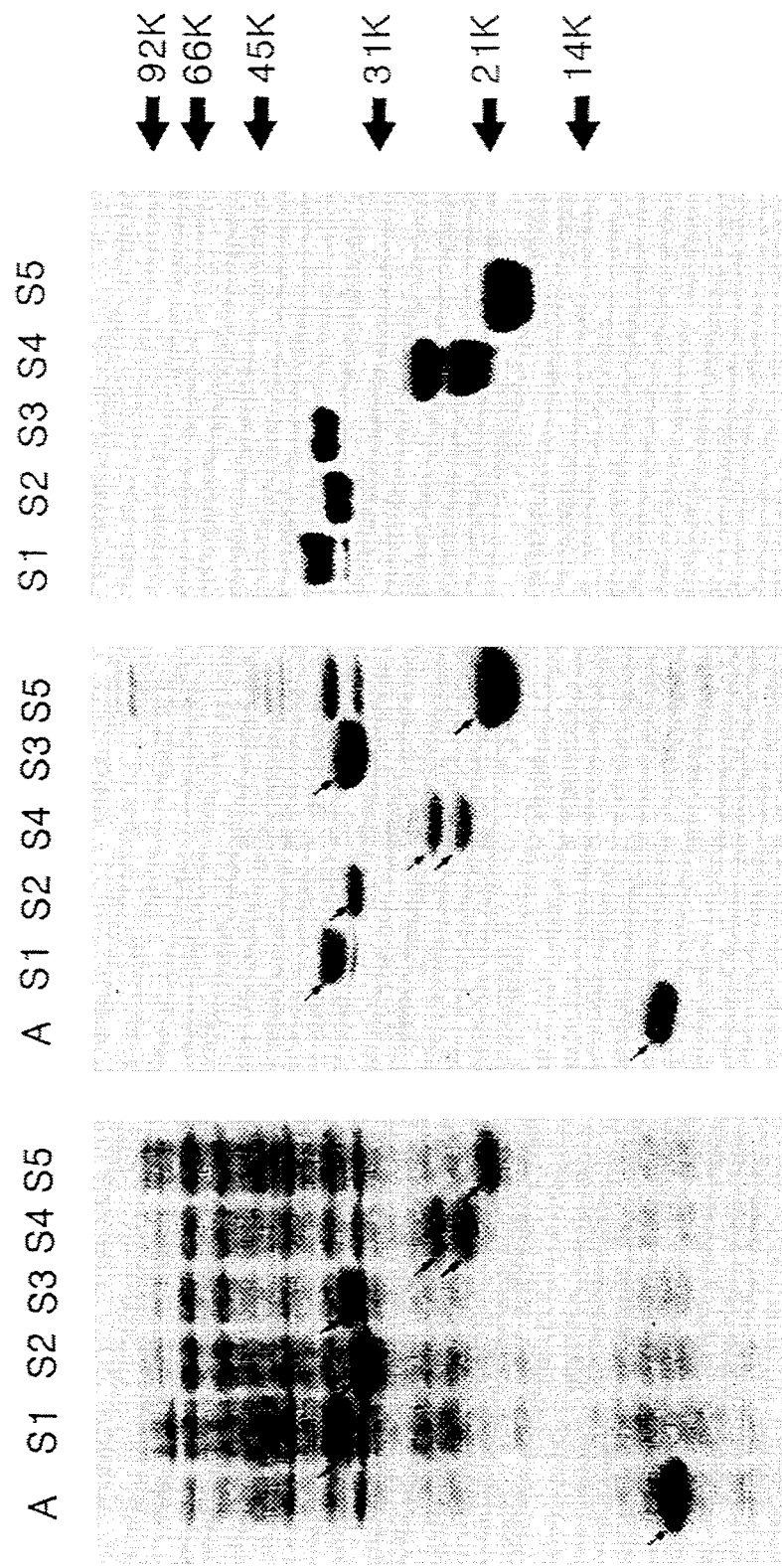

Yet another subject of the invention is the protein of the *pertussis* toxin in which the subunits S1, S2, S3, S4 have the amino acid sequences given in FIGS. 2 and 3. Further subjects of the present invention will become apparent from the description and the experimental examples which follow.

BRIEF DESCRIPTION OF THE TERMS USED IN THE DESCRIPTION

Genetic code: by this term is meant the relationship existing between the nucleotide sequence in DNA and the amino acid sequence in a protein.

An important characteristic of the genetic code is the fact that the synthesis of each amino acid is specified by a sequence of three nucleotides in the DNA, also called a triplet or codon.

The genetic code is universal, that is, a particular triplet codes the same amino acid in all living beings.

Reading phase or frame: by this term is meant a group of triplets used by a cell to decode the genetic message.

Cloning vectors: these are molecules of DNA which contain all the genetic information to enable them to replicate when transferred into a host micro-organism.

Examples of cloning vectors commonly used in genetic engineering are the plasmids and the DNA of several bacteriophages.

The plasmid DNA, which is circular, may be cut by suitable techniques and a heterologous DNA fragment may be inserted and the ring reclosed to form a larger molecule containing the heterologous DNA, the so-called molecule of recombinant DNA or hybrid plasmid.

The DNA of the bacteriophage may contain a segment of heterologous DNA inserted instead of several non-essential genes. Both these vectors are used for the insertion of heterologous DNA fragments and for the subsequent transformation of micro-organisms, also called host cells.

Restriction enzymes: these are hydrolytic enzymes capable of cutting a DNA molecule at specific sites, so-called recognition sites for the restriction enzymes.

Transposons: these are segments of DNA which may transpose and insert themselves at different points in the genome and give rise to the process known as transposition.

Promoter: a specific region of the DNA molecule in which the RNA polymerase starts transcription.

The promoter includes a recognition site and a binding site for the enzyme.

Termination Region: a specific region of the DNA molecule in which transcription ends.

Translation: this is the passage of genetic information from the mRNA to the protein according to the rules of the genetic code.

Expression: this term means the mechanism by means of which an organism can synthesise a protein coded by a specific gene.

In this case one says that the gene is expressed by the micro-organism.

In general, a method for obtaining a heterologous protein by recombinant DNA techniques requires the cloning of the gene which codes for the protein, where by cloning is meant the sequencing, isolation and purification of the gene and/or genes which code for the protein. Once cloned, the gene may be inserted in an expression vector and the molecule of recombinant DNA thus obtained may then be introduced into a hose micro-organism where the gene will replicate simultaneously with the replication of the micro-organism, from which it may be re-isolated by conventional methods.

With this method of operation it is possible to provide a continuously renewable source of the gene which can then be manipulated further, modified and inserted in other vectors or in different sites in the same vector.

The transformed micro-organism, grown in a suitable culture medium, will enable the protein coded by the gene to be synthesized.

Accordingly by the present invention there has been cloned and sequenced an Eco RI fragment of *Bordetella pertussis* BP 165 chromosomal DNA containing the genes which code for the five subunits of the *pertussis* toxin and the aminoterminal sequence of the subunits S1, S2, S3 and S4 of the *pertussis* toxin has been determined. In particular, the *pertussis* toxin produced by *Bordetella pertussis* 165 has been purified by affinity chromatography and the subunits subsequently separated by electrophoresis in polyacrylamide sodium dodecylsulphate gels as shown in FIG. 1.

The individual subunits were then separated and purified by electroelution (Hunkapiller M. W. et al.; Methods in Enzymology 91, 227–236, 1983) and analysed in a gas-phase microsequencer.

The aminoterminal sequence of the subunits S1, S2, S3 and S4 is given in FIG. 2.

A gene library was then constructed with the use of the *E. coli* lambda phase EMBL4 (bought from Promega Biotec 2800 S. Fish Hatchery Road, Madison, Wis. 53711 U.S.A.) starting from the strain *Bordetella pertussis* BP356.

This strain is a mutant which does not produce an active toxin and has a single transposon TN5 inserted in its chromosome [Weiss, A. A. et al. Infect. Immun. 42, 33–41 (1983)].

The chromosomal DNA of the said strain was separated from the cells and, after purification, was partially digested with the restriction enzyme Sau3A1 by the method and under the operative conditions described by Maniatis T. et al.: Molecular Cloning a Laboratory Manual Cold Spring Harbor N.Y., (1982). The fragments of chromosomal DNA with 15000 to 20000 base pairs were then separated and cloned in the *E. coli* lambda phage vector EMBL4 previously prepared as reported by Frischauf A. et al. [J. Mol. Biol. 170, 824–842 (1983)] with the use of the Promega Biotec "Packagene" Kit according to the method described by Maniatis T. et al. (Molecular Cloning a Laboratory Manual Cold Spring Harbor N.Y. 1982).

The recombinant phages were then used to transform *E. coli* NNM 539 cells (Promega Biotec).

The phages containing DNA fragments in which the transposon TN5 has been inserted where then selected from the transformed cells by the plate-hybridization technique with a radio-active probe for the TN5 DNA.

The recombinant phage DNA was then extracted from the positive recombinant phages and, after digestion with the restriction enzyme Eco-RI, the DNA fragments containing the transposon TN5 were separated and selected by hybridisation with a probe for TN5 DNA.

In this manner it was possible to isolate an Eco-RI DNA fragment with about 10500 base pairs containing the entire sequence of the transposon TN5 flanged on the one hand by about 1100 base pairs and on the other by about 3500 base pairs of chromosomal DNA of *Bordetella pertussis* BP 356.

The Eco-RI fragments with 10500 base pairs were then digested with the restriction enzyme Hinc II and the DNA fragments containing the junction between the TN5 and the chromosomal DNA were isolated by hybridisation with a probe for TN5 DNA.

Two fragments were thus identified, one with about 500 base pairs and the other with 1900 base pairs.

The two fragments, purified by electroelution, were then cloned in the phage vector M13mp8 (New England Biolabs) the DNA thereof had previously been cut by the restriction enzyme Hinc II.

The nucleotide sequences of the two fragments were then determined, starting from the Hinc II site according to the technique described by Sanger F. S.: Proc. Natl. Acad. Sci. 74, 5463 (1977).

The fragment with 1900 base pairs had at about 400 nucleotides from the Hinc II site, a nucleotide sequence (FIG. 3A from 3030 to 3100 bp) which, translated into the corresponding amino acids according to the genetic code, corresponded exactly to the amino acid sequence determined previously for the subunit S3 and given in FIG. 2.

This result confirms that the cloned DNA fragment with 10500 base pairs contained the gene for the *pertussis* toxin.

The fragment with 1900 bp was then used as a hybridization probe to identify and isolate a DNA fragment containing the gene for and/or which codes for the *pertussis* toxin from the chromosomal DNA of *B. pertussis* BP 165 for which a gene library had been constructed as described above for *B. pertussis* BP 356.

At the end of the cloning operations, a 4696 base-pair Eco RI fragment of chromosomal DNA was isolated which we knew contained at least the gene which codes for the subunit S3 in that the fragment hybridized with the specific probe for S3.

The said fragment or parts thereof were then cloned in the page vector M13mp8 and M13mp9 and the recombinant phage DNA thus obtained was sequenced.

Analysis of the sequences has enabled various open reading frames (ORFS) to be identified.

A comparison of their coding properties and the amino-terminal sequences of the subunits of the toxin have shown that four of these ORFS in fact code for the subunits S1, S2, S3 and S4 of the *pertussis* toxin.

Moreover, the molecular weight, the amino acid composition and the electric charges were in exact accordance with published data (Table 1). A fifth ORFS was also identified, placed between those which code for S4 and S3, which codes for a protein with a molecular weight and an amino acid composition identical to those described for the subunit S5.

These five open reading frames are grouped in a fragment with 3200 base pairs in the following order: S1, S2, S4, S5 and S3 and the ORFS reading frame which codes for S4 is superposed on those which code for S2 and S3 (FIG. 3). On the basis of these results it is possible to conclude that the sequences determined contain the genes which code for the subunits of the pertussis toxin, and hence the open reading frames will be termed genes below.

In accordance with the present invention a transcription signal, very similar to the concensus sequence for the *E. coli* promoters, was identified before the gene which codes for S1.

In fact a region—10, TAAAAT, which contains five of the six base pairs of the concensus sequence is associated with a region—35, TGCTGACC, which contains six of the eight bases of the concensus sequence—35.

The distance between the two regions—35 and—10 is 21 base pairs.

At the end 3' of the gene which codes for S3 there has been identified an inverted repeated sequence followed by a poly-T sequence which could represent a termination site.

Since no other promoter before the four genes S2, S3, S4 and S5 has been identified in the DNA fragment it may be deduced that these genes are organized in a single operon and are transcribed as a single polycistronic mRNA.

The presence of a single Shine-Dalgarno sequence located nine base-pairs before the ATG of the gene S1, strongly suggests that this is the ribosomal binding site which enables the translation of the S1 mRNA.

The presence of a new consensus sequence, TCC (T) GG, located eight to twelve base pairs before each ATG initiation codon for the four genes, suggests that this site is responsible for the translation of the entire mRNA.

Moreover it was found that the gene S4, which is produced in stoichiometric quantities of 2 to 1 with respect to the other genes, is the only one which is preceded by a slightly modified consensus sequence, TCCTGG, which probably increases the translation efficiency.

A characteristic common to all the subunits of the *pertussis* toxin is the presence, in the gene, of a sequence immediately preceding the mature protein, which codes for a 27-42 amino acid peptide the characteristics of which are typical of signal peptides involved in the secretion of the proteins.

This suggests that the various subunits are synthesized as proproteins, processed and secreted individually in the periplasmic space and subsequently processed, assembled and released into the extra-cellular space in the form of a single protein.

It has also been found that the signal peptide for S4 is unexpectedly long (42 amino acids) and has the highest aminoterminal positive charge described until now.

Since the positively-charged aminoterminal regions play an important role in the efficiency of production of the secreted proteins, the unusual structure of the signal peptide for S4 could cause increased translation of the gene S4.

It was also noted that, in the absence of the subunit S3 as occurs in the mutant BP356, the *pertussis* toxin is not excreted into the culture medium. Consequently, this protein is necessary for the complete assembly of the *pertussis* toxin.

The cloned DNA fragment or further fragments thereof, the said fragments containing at least one gene which codes for at least one subunit of the *pertussis* toxin, must be capable of being inserted in an expression vector and the hybrid plasmid thus obtained may be used to transform a micro-organism.

The transformed micro-organisms, grown in a suitable culture medium, are able to express the DNA fragment or fragments thereof by synthesis of the *pertussis* toxin or one or more subunits of the *pertussis* toxin.

Cloning vectors suitable for the purpose may be selected from natural plasmids known in the art or synthetic vectors obtained by recombinant DNA techniques.

In particular, the plasmid of *E. coli* pEMBL8 with about 4000 base pairs is used, this containing the gene for resistance to ampicillin and restriction sites useful for the cloning such as: HindIII, PstI, AccI, HincII, SalI, BamHI, AvaI, SmaI, XmaI, EcoRI (Dente L. et al (Nucleic Acids Research, 11, 1645≠1655 (1983)), and the plasmids 31A, 31B and 31C derived from the vector PEX29 (Klinkert M. et al. Inf. Imm. 49, 329-335 (1985)) which contain the gene which codes for the DNA polymerase of the page MS2 placed under the control of the inducible promoter pL and a polylinker inserted before the end of the gene of the MS2 polymerase in three possible frames, so as to be able to break each possible DNA fragment in the same frame of the MS2 polymerase.

Examples of micro-organisms used as host cells are strains of *Escherichia coli, Bacillus subtilis,* Saccharomyces, or eucaryotic cells.

In accordance with the present invention, there are used cells of *E. coli* JM 101 (New England Biolabs 32 Tozer Road, Beverly, Mass. 01915-9990 U.S.A.) and cells of *E. coli* K-12 H1 trp (described by Remant E. Gene 15: 81-93 (1981)) which produce a heat-sensitive repressor which, at 30°, completely inhibits the transcription of the gene of the MS2 polymerase preventing the production of proteins fused to it and, at 42° C., is inactivated giving good production of the polymerase and of the proteins fused to it.

The choice of the cloning vector and of the micro-organism to be transformed are not however limited by the present invention.

In accordance with the present invention, the 4696 base-pair fragment of the chromosomal DNA obtained as described above, was inserted in the plasmid vector of *E. coli* pEMBL-8 after digestion of the plasmid DNA with the restriction enzyme Eco RI.

The hybrid plasmid obtained, designated pPT101, was then used to transform cells of *E. coli* JM101 (New England Biolabs) made competent by the method described by Cohen S. et al. (Proc. Natl. Acad. Sci. U.S. 69, 2110 (1972)).

The strain of *E. coli* (pPT101) was desposited in the American Type Culture Collection, on Jun. 8, 1985 with the number ATCC 67854 as a substitute for ATCC 53212.

In order to check the ability of the transformed micro-organism to express the cloned DNA, fragment, the *E. coli* strain (pPT101) was cultivated in a suitable culture medium.

More particularly, the strain was grown in LB medium (DIFCO) at a temperature of 37° C. up to an absorbance of 0.75, measured in the culture broth at 590 nm.

The cells were then subjected to lysis and the *pertussis* toxin was determined directly in the cellular lysate by immunoenzymatic methods.

The biological activity of the *pertussis* toxin was determined by the method reported by Hewlett E. L. et al. (1983) (Infect. Immun. 40, 1198-1203), the change in form of the CHO cells incubated with the cellular lysate under examination being analysed.

The results obtained confirm that the 4696 base-pair fragment of *Bordetella pertussis* chromosomal DNA contains the genes which code for the five subunits of the *pertussis* toxin and the said toxic can be neutralized by antibodies against the toxin itself.

According to one embodiment of the present invention, the genes which code for the individual subunits of PT were cloned in the plasmids 31A, 31B, 31C derived from the vector PEX29 and the hybrid plasmids thus obtained and designated PTE255 (S1), PTE211 (S2), PTE221 (S3), PTE240 (S4) and PTE230 (S5) were used to transform cells of *E. coli* K-12 H1 trp.

The cells thus transformed were then cultivated in a suitable culture medium and the subunits, obtained as fused proteins were recovered, purified and tested to determine their biological activities.

The results obtained show that all five subunits, when injected into rabbits, induce the formation of specific antibodies.

Moreover, the fused S1 protein shows the same enzymatic activity as the entire PT toxin, thus showing not only an immunological but also a functional identity with the natural S1.

In fact ADP-ribosylation tests carried out by incubating fused S1 with homogenized ox retina (ROS) in the presence of NAD marked with $^{32}P$, indicate that the subunit S1 binds the ADP-ribose group to the transducine present in the retina.

Figures 11, 12:
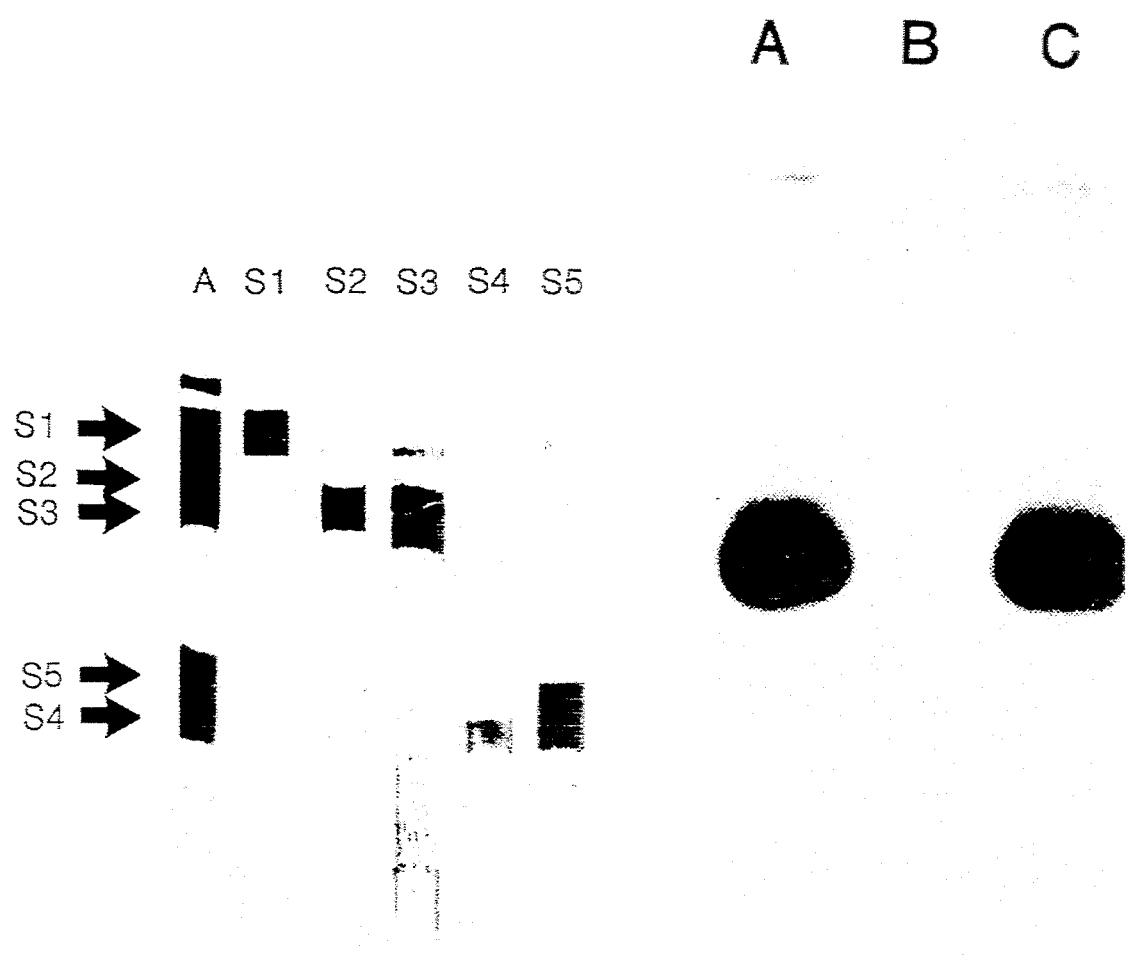

Hence both the *pertussis* toxin and the individual subunits obtained by the method of the present invention may be used for the preparation of vaccines against *pertussis* and diagnostic kits for determining specific antibodies in clinical samples from individuals infected with *pertussis.*

Analysis of the sequences given in the present invention also shows a certain similarity between the amino acid sequence in the subunit S1 of the *pertussis* toxin and that of the subunit A of the cholera toxin (J. Mekalanos et al. Nature 306, 551–557, 1983(FIG. 7).

There is thus a possibility of preparing a vaccine capable of neutralizing cholera and *pertussis* simultaneously, with the use of the peptide S1 made by chemical synthesis or by recombinant DNA techniques.

BRIEF DESCRIPTION OF THE DRAWINGS

FIG. 1: Electrophoresis of the *pertussis* toxin purified by affinity chromotography on 15% polyacrylamide (PAGE)-sodium dodecylsulphate (SDS) gel.

The toxin in column A was treated with a reducing agent before being applied to the gel.

The toxin in column B was not reduced.

S2 and S3, although have the same deduced molecular weight (table 1—data from literature), had different mobilities on SDS-PAGE.

S5 was slightly coloured and also, having a lower molecular weight than that of S4 (table 1—data from the literature), under reducing conditions migrated more slowly than S4.

FIG. 2: Aminoterminal sequence of the subunits S1, S2, S3 and S4 determined by means of a microsequencer in the gaseous phase with the use of the individual subunits purified as in FIG. 1.

A=alanine; C=cysteine, D=aspartic acid; E=-glutamic acid; F=phenylalanine; G=glycine; H=histidine; I=isoleucine; K=lysine; L=leucine; M=methionine; N=asparagine; P=proline; Q=glutamine; R=arginine; S=serine; T=threonine; V=valine; W=tryptophan; Y=tyrosine; X=unidentified amino acid residue.

All the sequences given are exactly in accordance with the nucleotide sequences with the single exception of the glutamine-2 in S2 which was found to be a threonine (FIG. 3).

FIG. 3A: Nucleotide sequence of the Eco RI fragment containing the five genes which doe for the *pertussis* toxin.

The amino acid sequence of the give subunits of the *pertussis* toxin deduced from the nucleotide sequence is also given.

The arrows, before the amino acid sequences, indicate the start of the mature subunits as identified by comparison with the aminoterminal sequences in FIG. 2.

In the case of S5, the arrow indicates the expected start of the mature subunit.

Before the sequence of each subunit, the amino acid sequence of the expected peptide signals is given.

Upstream of the gene which codes for S1 are indicated the expected promoter and Shine-Dalgarno sequences.

The sequences TCC (T) GG are present before S2, S3, S4 and S5.

At the end of the gene which codes for S3 the arrows above the nucleotide sequence indicate an inverted repetitive sequence followed by a poly-T sequence (underlined) which represents a possible transcription termination site.

Four open reading frames (ORFS) having the same use as the codons of the genes of the *pertussis* toxin are indicated by dotted lines.

FIG. 3B: Schematic representation of the ORFS frames in the sequence given in FIG. 3A.

The frames 1, 2 and 3 are shown from top to bottom and only the open reading frames with at least 200 base pairs are given.

P: expected promoter sequence

T: expected terminator sequence

FIG. 4: Amino acid sequence of the signal peptides of the five subunits of the *pertussis* toxin.

The sequence (S) (P) A×A precedes the site at which cutting occurs.

FIG. 5A: Translation and transcription signals. The initiation ATGs of the codons of the various ORFS are aligned and shown to the right.

Upstream of the ATG of S1 are shown the expected promoter and Shine Dalgarno sequences.

The respective sequences of *E. coli* are given above.

Upstream of the ATG of the other ORFS is given the sequence TCC (T) GG.

This sequence was not identified before the other ATG codons present in the entire nucleotide sequence given in FIG. 3.

FIG. 5B: This gives the structure of the expected termination sequence.

FIG. 6: This shows the correspondence between the amino acid sequences of S2 and S3. The arrows indicate the sites at which the preproteins are cut and the start of the matured subunits.

FIG. 7: Comparison of the amino acid sequence of the subunit S1 of the *pertussis* toxin and the subunit A of the cholera toxin. The corresponding amino acids in the two proteins are bracketed.

FIG. 8: The three plasmids 31A, 31B, and 31C and the introduction of the polylinker into the three possible frames are shown.

FIG. 9: This shows the cloning scheme for the genes which code for the five subunits of the *pertussis* toxin in the plasmids 31A, 31B and 31C and the construction of the hybrid plasmids PTE255 (S1), PTE211 (S2), PTE221 (S3), PTE240 (S4) and PTE230 (S5).

FIG. 10A: This shows the electrophoresis of the total lysate of the strains which produce the polymerase of MS2 and the five subunits fused thereto (S1–S5).

FIG. 10B: Electrophoresis of the partially-purified, fused proteins (S1, S2, S3, S4 and S5) on 15% acrylamide gel.

FIG. 10C: Electrophoresis of the purified fused proteins (S1, S2, S3, S4, S5) on 15% acrylamide gel.

FIG. 11 shows:

A): Western blot of the *pertussis* toxin incubated with goat serum against the entire toxin; this serum reacts with all five subunits;

B): Western blot of PT incubated with anti-fused S1 anti-serum: only the subunit S1 detected;

C): Western blot of PT incubated with anti-fused S2 anti-serum: only the subunit S2 detected;

D): Western blot of PT incubated with anti-fused S3 anti-serum: only the subunit S3 detected;

E): Western blot of PT incubated with anti-fused S4 anti-serum: only the subunit S4 detected;

F): Western blot of PT incubated with anti-fused S4 anti-serum: only the subunit S5 detected;

FIG. 12: Autoradiography on polyacrylamide gel indicating enzymatic activity of: lane A, *pertussis* toxin; lane B, the absence of *pertussis* toxin results in no mark; and lane C, fused S1;

FIG. 13: Nucleotide sequence of the DNA region which contains genes of the *pertussis* toxin. The sequence at the center is that of *Bordetella pertussis* while above and below respectively are given the differences found in the sequences of *B. bronchiseptica* and *B. parapertussis.*

FIG. 14: Southern blot showing that *Bordetella pertussis* may be distinguished from *B parapertussis* and *bronchiseptica* (lane C) by the magnitude of the Eco RI fragment which hybridises with the clone pPT101.

FIG. 15: Amino acid sequence of the five subunits of the *pertussis* toxin. The sequence at the center is that of *Bordetella pertussis* while above and below respectively are given the differences found in *B. bronchiseptica* and *B. parapertussis.*

FIG. 16: Enzymatic activity of the subunit S1 produced in *E. coli* as the fusion protein.

A: S1 of *B. pertussis*

B: MS2 polymerase from the vector pEX31a

C: Subunit S3

D: S1 of *B. parapertussis*

E: S1 of *B. bronchiseptica*

TABLE 1

Comparison of the amino acid composition in percentages, molecular weights and total charges of the five subunits of the pertussis toxin. A: experimental data given by Tamura et al. (Biochem. 21, 5516-5322 (1982)). B: Data deduced from the nucleotide sequence.

| | S1 | | S2 | | S3 | | S4 | | S5 | |
|---|---|---|---|---|---|---|---|---|---|---|
| | A | B | A | B | A | B | A | B | A | B |
| Ala | 10.6 | 11.5 | 6.5 | 6.0 | 11.7 | 11.0 | 9.4 | 8.1 | 9.8 | 8.0 |
| Arg | 5.9 | 9.3 | 6.2 | 6.0 | 6.1 | 6.5 | 5.1 | 5.4 | 3.3 | 3.0 |
| Asp + Asn | 9.3 | 9.4 | 6.3 | 6.5 | 6.3 | 6.0 | 5.3 | 4.5 | 8.2 | 8.1 |
| Cys | 1.0 | 0.8 | 1.3 | 3.0 | 1.1 | 3.0 | 0.9 | 3.6 | 1.6 | 4.0 |
| Gly | 11.2 | 7.2 | 13.0 | 10.5 | 11.9 | 10.0 | 9.6 | 6.3 | 8.7 | 8.0 |
| Glu + Gln | 10.6 | 10.2 | 8.7 | 7.5 | 9.0 | 8.0 | 9.5 | 8.2 | 9.3 | 9.1 |
| His | 1.7 | 2.1 | 2.4 | 2.0 | 1.0 | 1.0 | 0.5 | 0.9 | 3.0 | 3.0 |
| Ile | 3.2 | 3.8 | 4.2 | 5.5 | 5.0 | 6.5 | 2.0 | 1.8 | 3.4 | 3.0 |
| Leu | 5.5 | 3.4 | 7.3 | 7.5 | 8.1 | 8.0 | 8.4 | 9.0 | 13.8 | 15.1 |
| Lys | 2.2 | 0.0 | 3.4 | 3.0 | 2.7 | 2.5 | 6.9 | 7.3 | 4.7 | 5.0 |
| Met | 1.6 | 2.1 | 1.5 | 1.5 | 1.1 | 1.5 | 5.1 | 7.2 | 1.6 | 2.0 |
| Phe | 3.5 | 3.0 | 3.2 | 2.5 | 3.2 | 2.5 | 3.6 | 4.5 | 4.9 | 5.0 |
| Pro | 4.4 | 3.8 | 4.6 | 4.5 | 5.7 | 5.0 | 9.1 | 10.0 | 5.6 | 5.0 |
| Ser | 10.6 | 9.4 | 8.5 | 8.5 | 6.3 | 5.0 | 8.0 | 5.4 | 6.9 | 6.0 |
| Thr | 7.4 | 7.2 | 10.4 | 10.0 | 8.2 | 8.0 | 5.0 | 4.5 | 6.9 | 7.0 |
| Trp | — | 0.8 | — | 1.0 | — | 0.5 | — | 0.0 | — | 1.0 |
| Tyr | 4.6 | 8.0 | 7.6 | 8.0 | 7.9 | 9.5 | 2.2 | 1.8 | 4.3 | 4.0 |
| Val | 6.7 | 7.6 | 4.9 | 6.0 | 4.7 | 5.0 | 9.4 | 10.9 | 4.0 | 3.0 |
| MW[a] | 28.0 | 26.22 | 23.0 | 21.92 | 22.0 | 21.86 | 11.7 | 12.06 | 9.3 | 10.94 |
| pI:charge[b] | 5.8 | −4.0 | 8.5 | +2.0 | 8.8 | +3.0 | 10.0 | +5.0 | 5.0 | −3.0 |

[a]Molecular weight in kilodaltons

[b]In order to compare the entire charge of the subunits, we have given the experimental isoelectric point at A and the net charge calculated for each subunit at B.

The net charge is calculated as ((Lys+Arg)−(-Glu+Asp)).

The experimental examples which follow are illustrative and non-limiting of the invention.

EXAMPLE 1

Determination of the Aminoterminal Sequence of the Subunits of the *pertussis* Toxin A strain of *B. pertussis* BP165 was grown in a fermentor (Palias System N.B. App. Fabr. Van door De Bilt), provided with an agitator, with a capacity of 50 l, containing 40 l of Verwey culture medium with the following composition:

| | |
|---|---|
| Bacto casamino acids (DIFCO) | g. 14 |
| KCl | g. 0.2 |
| $K_2PO_4$ | g. 0.5 |
| $MgCl_2.6H_2O$ | g. 0.1 |
| nicotinic acid | g. 0.02 |
| glutathione | g. 0.01 |
| Starch | g. 1.00 |
| $H_2O$ | 1 liter |
| pH 6.8 | | previously sterilized at 120° C. for 15 minutes, under aeration, at a temperature of 36.5° C. for 28 hours.

At the end of the said period of time, the cells were separated from the culture broth by centrifuging and the *pertussis* toxin was recovered from the supernatant liquid by affinity chromotography on Affi-Gel blue (100-200 mesh) by BioRad and on fetuin-sepharose as described by Sekura R. D. et al. [The J. Biol. Chem. 258, 23, 14647-14651 (1983)].

The protein obtained had a purity of more than 95%.

The protein was then subjected to electrophoresis on a 15% (p/p) polyacrylamide gel containing sodium dodecylsulphate (SDS) at 125 volts for 5 hours and the five subunits were separated, as given in FIG. 1.

Each of these bands was cut and subjected to electroelution by the method of Hunkapiller M. W. et al ([Methods in Enzymology 91, 227-236(1983)].

Thus the five purified subunits were obtained.

The aminoterminal sequence of each of the subunits obtained was determined subsequently with the use of a gaseous-phase micro-sequencer model 470A (Applied Biosystems, Foster City, Calif.—U.S.A.) in accordance with the operating instructions.

FIG. 2 shows the aminoterminal sequence of the subunits S1, S2, S3 and S4.

EXAMPLE 2

Cloning of the DNA Fragment Containing the Genes Which Code for the Five Subunits of the *pertussis* Toxin The strain *B pertussis* BP 356 is a mutant strain containing a transposon (TN5) inserted in the chromosome.

The strain, described by Weiss A. A. et al. in Infect. Immun. 42, 33–41 (1983), was produced by Stanley Falkow, Stanford University.

A culture of *B pertussis* BP 356 in the exponential phase (100 ml of Verwey medium) was centrifuged and the cells resuspended in 2 ml of 25% sucrose, 50 mM Tris, 1 mM EDTA (pH8).

To the suspension were then added 50 μl of lysozyme (40 mg/ml) and, after 5 minutes, 10 μl of proteinase K (20 mg/ml).

To the agitated suspension were added 0.4 ml of EDTA (0.05M).

The cells were subjected to lysis by the addition of 0.25 ml of Sarkosil (10%) at 0° C. to the cell suspension.

The lysated cells were then suspended in 35 ml of a solution containing 69.6 g of CsCl in 55.2 ml of buffer, 50 mM Tris, 1 mM EDTA (pH8) containing 50 μg of phenyl methyl sulphonylfluoride, an inhibitor for the proteinase K. The solution was then centrifuged at 50,000 revolutions per minute (rpm) for 16 hours in a 70 t i Beckmann SOV t i and the chromosomal DNA thus separated was then recovered as a viscous band. 500 μg of chromosomal DNA thus obtained were dialyzed against 100 ml of distilled water to remove the CsCl and then partially digested with five units (U) of restriction enzyme Sau 3 A1 (Boehringer) in 5 ml of 50 mM NaCl, 10 mM Tris, 10 mM $MgSO_4$, 1 mM dithiothreitol buffer (pH7.4).

The digested DNA was precipitated by the addition to the solution of 12 ml of ethanol and, after separation, was resuspended in 0.5 ml of 10 mM Tris, 1 mM EDTA buffer.

This volume was loaded on to a 10% to 40% gradient of sucrose dissolved in 35 ml of 1 mM NaCl, 10 mM Tris, 1 mM EDTA buffer (pH 7.5).

The gradient was then centrifuged at 26000 rpm for 16 hours in a Beckman SW 28 rotor.

After this, 1 ml fractions were collected and the molecular weight of the DNA content of each fraction was determined by electrophoresis in agarose, as reported by Maniatis T. et al. "Molecular Cloning a Laboratory Manual", Cold Spring Harbor N.Y. (1982).

The fractions containing the DNA fragments with 15000–20000 base pairs (bp) were then dialyzed and the DNA precipitated with ethanol as described above.

The precipitated DNA was separated by centrifuging and resuspended in 100 μl of 10 mM Tris, 1 mM EDTA buffer (pH 7.5) to a final concentration of 1 μg/ml of DNA.

The chromosomal DNA fragments were then cloned.

This was carried out with the use of an *E. coli* lambda phage vector EMBL 4 prepared as described by Frishauf A. et al. J. Mol. Biol. 170, 827–842 (1983).

1 μg of DNA of the phage vector EMBL 4, previously cut with two U of restriction enzyme Bam HI, and 1 μl of the solution containing the fragments of DNA with 15000–20000 bp were mixed in 5 μl of 1 mM ATP, 20 mM Tris, 10 mM $MgCl_2$, 10 mM dithiothreitol buffer (pH 7.6) in the presence of one U of T4 DNA ligase.

The ligase reaction was carried out at a temperature of 15° C. for 16 hours.

At the end of this period, the recombinant DNA obtained was inserted in lambda phages without DNA, with the use of the Packagene Kit of Promega Biotec (Maniatis T. et al. Molecular Cloning a Laboratory Manual Cold Spring Harbor N.Y. (1982)).

The recombinant phages thus obtained were used to transform the strain *E. coli* strain NM 539 (Promega Biotec.).

The transformed cells of *E. coli* NM 539 were plated on LB medium (Bacto Triptone 10 g, Bacto Y.E. 5 g, NaCl 10 g, $H_2O$ 1 liter pH 7.5) giving about 30000 plates of recombinent phages.

About 5000 recombinant phages were hybridized by hybridization on a plate with a radioactive probe for the TN5 DNA, in order to identify those phages containing the DNA fragment in which the transposon TN5 was inserted.

Twelve recombinant phages were positive on hybridization. The DNA was then extracted from these phages by the extraction methods given above.

1 μg of recombinant phage DNA was cut with two U of the restriction enzyme Eco RI in 20 μl of 50 mM Tris, 100 mM NaCl, 10 mM $MgSO_4$ buffer (pH 7.4), the solution being kept at a temperature of 37° C. for one hour.

The digested solution of DNA was then loaded on to a 1% agarose gel and subjected to electrophoresis for two hours at 120 volts for six hours.

The fragments of recombinant phage DNA thus separated were transferred on to nitrocellulose and hybridized with a radioactive probe for TN5 DNA in order to identify the Eco RI fragment containing the transposon TN5.

In this manner a positive Eco RI fragment of about 10500 bp was isolated which contained the entire sequence of TN5 flanged on one side by about 1100 bp and on the other by about 3500 bp of chromosomal DNA of *B. pertussis* BP 356.

1 μg of the Eco RI fragment was cut with two U of the enzyme Hinc II in 25 μl of 50 mM NaCl, 10 mM Tris, 10 mM $MgSO_4$, 1 mM dithiothreitol buffer (pH 7.4), at 37° C. for 1 hour).

At the end of this period, the solution containing the digested DNA fragments was subjected to electrophoresis on 1% agarose gel for six hours at 120 volts, transferred onto nitrocellulose and then hybridized with the radioactive probe for TN5 DNA, in order to identify the fragments containing the junction between the TN5; and the chromosomal DNA.

Thus two fragments were identified, one with about 500 bp and the other with about 1900 bp.

The two fragments were then purified by electroelution and cloned in the page vectors M13 mp8 and M13 mp9 (New England) the DNA of which had previously been cut with the restriction enzyme Hinc II.

The nucleotide sequence of the two fragments was then determined starting from the Hinc II site with the use of the technique described by Sanger F. S. (Proc. Natl. Acad. Sci. 74, 5463 (1977)).

At about 400 nucleotides from the HincII site of the larger fragment (1900 bp), the nucleotide sequence given in FIG. 3A—from 3030 to 3100 bp was identified and, translated into the corresponding amino acids, gave the amino acid sequence determined by us for the subunit S3 as described in Example 1 and given in FIG. 2.

This result indicates that, in the strain *B. pertussis* 356, the TN5 is inserted in the gene which codes for the subunit S3 of the PT and confirms that the fragment of DNA cloned by us contains the gene for the *pertussis* toxin.

The fragment thus identified was then used as a hybridization probe to identify the gene for the PT present in the chromosomal DNA of *B. pertussis* BP165.

A gene library was again constructed for this strain in the phage vector EMBL 4, in the same manner as described for *B. pertussis* BP 356.

At the end of the cloning operation, an Eco RI fragment was isolated with 4696 bp which we knew contained at least the gene which codes for the subunit S3 in that it hybridized with the specific probe S3.

In order to check whether this fragment also contained the genes which code for the other PT subunits, the fragment, or parts of it, were cloned in the phage vectors M13 mp8 and M13 mp9 and then the nucleotide sequence of the entire fragment was determined.

Analysis of the nucleotide sequence of the entire fragment, given in FIG. 3, shows that this fragment also contains the genes which code for the subunits S1, S2 and S4, in that the translation of the nucleotide sequence of the DNA fragment in the corresponding amino acid sequence corresponds to the amino acid sequences determined by us for the subunits S1, S2 and S4 and given in FIG. 2.

Once the beginning of the amino acid sequence had been identified from the data given in FIG. 2, it was possible to deduce the entire amino acid sequence of the said subunits.

The analysis of the chemical and physical properties of the various subunits deduced from the amino acid sequence, such as the molecular weight, amino acid composition and electric charge, are in accordance with the data in the literature (Tamura et al. (1982) Biochemistry 21, 5516–5522).

It was also noted that a common characteristic of all five subunits was the presence in the gene of a sequence immediately before the mature protein which coded for a peptide with 27–42 amino acids and which had characteristics typical of the peptides involved in the secretion of the proteins, that is the presence of one or more positive charges on the terminal amino group followed by a hydrophobic zone (FIG. 4).

This shows that the subunits were produced in the form of preproteins and these were subsequently processed during secretion.

All the secretion signals also terminated with the sequence (S) (P)A×A which is typical of other secretion signals.

Among the genes which code for S4 and S3 was also identified a nucleotide sequence, from 2461 to 2862 bp, which codes for a peptide which has the same properties as the other secretion signals and terminates with the sequence SPADVA, followed by an amino acid sequence which has exactly the same amino acid composition as that given in the literature for the subunit S5 (Table 1).

This has enabled us to establish that the Eco RI fragment with 4696 bp cloned by us also contains the gene for the subunit S5 and hence has enabled us to determine the amino acid sequence of the latter (FIG. 3).

Further analysis of the nucleotide sequence of the DNA fragment isolated and cloned by us has enabled the location of a promoter in the zone 440 bp to 485 bp, which has the same characteristics as those of *E. coli*, and of a termination sequence in the zone 3608 to 3670 bp.

This means that the five genes of the *pertussis* toxin are organised in a typical bacterial operon and are transcribed in a single mRNA.

EXAMPLE 3

Construction of the Hybrid Plasmid pPT 101 Containing the Genes Which Code for the *pertussis* Toxin 1 $\mu$g of plasmid DNA of *E. coli* pEMBL-8 described by Dente L. (1983) Nucl. Acids Res. 11, 1645–1655 containing the gene which gives resistance to ampicillin were cut with two U of Eco RI enzyme in 20 $\infty$l of 100 mM NaCl, 50 mM Tris, 10 mM MgSO$_4$ buffer (pH 7.4) at 37° C. for one hour.

At the end of the digestion reaction, 3 $\mu$g of the Eco-RI DNA fragment with 4696 bp, the sequence of which is given in FIG. 3, were added to the solution containing the cut plasmid DNA and reacted in the presence of one U of T4 DNA ligase (BRL) under the conditions recommended by the manufacturer.

The ligase mixture was then used to transform cells of ampicillin-sensitive *E. coli* JM 101 (New England Biolabs) rendered competent.

The transformed cells were selected on LB plates containing 100 $\mu$g/ml of ampicillin in order to isolate those cells which contain the hybrid plasmid.

Among the clones of ampicillin-resistant (Amp$^R$) *E. coli* thus obtained, it was possible to isolate clones containing the hybrid plasmid pEMBL 8 containing the DNA fragment which codes for PT by the technique of hybridization with a probe for the sequence of the PT gene.

One of these hybrid plasmids were designated pPT 101 by us.

The *E. coli* JM 101 strain containing the plasmid has been deposited by us at the American Type Culture Collection under ATCC-67854 as a substitute for ATCC-53212.

EXAMPLE 4

Construction of the Hybrid Plasmid PTE 255 Containing the Gene Which Codes for the Subunit S1

The construction of the hybrid plasmid was carried out in the manner given in example 3 above, by ligating the plasmid 31B, previously digested with the restriction enzymes Bam HI and Xba I, with the Sau3a1-Xba I from 612 to 1317 of the 4696 bp fragment corresponding to the gene which codes for S1.

The ligase mixture was then used to transform cells of competent *E. coli*, the transformed cells being selected on LB plates (DIFCO) containing ampicillin.

The hybrid plasmid PTE 255 (S1) was separated from one of the positive clones and its sequence is given in FIG. 9 where the lower case letters indicate the coding sequence for the polymerase MS2 and the upper case letters indicate the sequence which codes for S1.

The resulting protein contains all the subunit S1 apart from the first amino acid Asp.

EXAMPLE 5

Construction of the Hybrid Plasmid PTE 211 Containing the Gene Which Codes for the Subunit S2

This was carried out as in Example 3 above with the use of the plasmid 31A digested with Bam HI and treated with DNA polymerase to fill the cohesive termini and the Sau96-SmaI fragment from 1433 to 2064 of the 4696 bp fragment, corresponding to the gene which codes for S2, was treated with DNA polymerase (Klenow) to fill the cohesive termini.

The hybrid plasmid PTE 211 (S2) isolated from one of the positive transformants had the sequence given in FIG. 9.

The resulting fused protein contained the sequences of the polymerase of MS2 (lower case letters to the left) fused to an amino acid of the peptide leader of the subunit S2 (upper case letters), and hence to the protein S2 (lower case letters to the right).

EXAMPLE 6

Construction of the Hybrid Plasmid PTE 221 Containing the Gene Which Codes for the Subunit S3

This was carried out as in Example 3 above with the use of the plasmid 31C digested with Bam HI and treated with DNA polymerase to fill the cohesive termini and the SphI-DdeI fragment from 3014 to 3628 of the 4696 bp fragment, corresponding to the gene which codes for S3, was treated with DNA polymerase to eliminate the cohesive termini.

The hybrid plasmid PTE 221 (S3) isolated from one of the positive transformants had the sequence given in FIG. 9.

The fused protein which resulted from it contained the polymerase MS2 (lower case letters to the left) fused to five amino acids of the peptide leader of the subunit S3 (upper case letters), and hence to the natural subunit S3 (lower case letters to the right).

EXAMPLE 7

Construction of the Hybrid Plasmid PTE 240 Containing the Gene Which Codes for the Subunit S4

This was carried out as in example 3 above, with the use of the plasmid 31B cut with Bam HI and treated with polymerase and the BstN1—BstN1 fragment from 2151 to 2600 of the 4696 bp fragment corresponding to the gene which codes for S4.

The sequence of the hybrid plasmid PTE 240 (S4) thus obtained is given in FIG. 9.

The fused protein which results form it contains the polymerase of MS2 (lower case letters) fused to two amino acids of the peptide leader of the subunit S4 (upper case letters), and hence to the natural subunit S4.

EXAMPLE 8

Construction of the Hybrid Plasmid PTE 230 Containing the Gene Which Codes for the Subunit S5

This was carried out as in Example 3 above, with the use of the plasmid 31A cut by Bam HI and treated with DNA polymerase to fill the cohesive termini and the Aat2-SnaBI fragment from 2558 to 3210 of the 4696 bp fragment, corresponding to the gene which codes for S5.

The sequence of the hybrid plasmid PTE230 obtained is given in FIG. 9.

The resulting fused protein contained the polymerase of MS2 (lower case letters to the left), two amino acids of the peptide leader of the subunit S5 (upper case letters), and hence the natural subunit S5 (lower case letters to the right).

EXAMPLE 9

Production of *pertussis* Toxin and Experiment to Determine Its Activity

The strain *E. coli* JM 101 (pPT 101) was grown in a 100 ml flask containing 10 ml of LB, under mild agitation, at a temperature of 37° C. for 16 hours.

0.1 ml of this culture was then used to innoculate 10 ml of LB medium and grown at 37° C. up to an absorbance $OD_{590}$ of 0.75.

The culture broth was then centrifuged at 4° C. and the cells thus separated were resuspended in 0.5 ml of 10 mM Tris (pH 7.5).

The cell suspension was subjected to lysis by ultrasonics in a Branson Sonifier-cell Disruptor 200 (Bransonsonic Power Co., a Smithkline Company).

The presence and biological activity of the *pertussis* toxin were ten determined directly on the cellular lysate by means of CHO cells, by the method reported by Hewlett, E. L. et al. (1983) Infect. Immun. 40, 1198-1203. The CHO cells used were obtained in our laboratory by mutation of CHO ATCC CCL 61 cells. 10,000 CHO cells were incubated in 2.5 ml of medium (the composition of which is given by Hewlett E. L. et al. (1983) (Infect. Immun. 40, 1198-1203) in the presence of 5 μl of cell extract of *E. coli* JM 101 (pPT 101), 5 μl of *E. coli* JM 101 cells containing the unmodified plasmid PEMBL-8 and 0.1 ng of *pertussis* toxin as a standard.

Part of the cell extract had previously been incubated with a 1:100 dilution or ordinary goat antiserum (A) and another part with 1:100 dilution of the same goat antiserum taken after immunization with the *pertussis* toxin.

After 48 hours of incubation at 37° C., the results were read in the manner described by Hewlett in the text indicated above.

A value of 4 (+) was attributed to a maximum form change of the CHO cells, a value of 1 (+) to a minimum form change and (−) to a lack of form change.

The results are given in table 2.

TABLE 2

| Sample | Activity on CHO cells of the toxin produced by the recombinant clones: Whole | Goat anti-toxin antibodies | Preimmune goat antibodies |
|---|---|---|---|
| 0.1 ng Toxin | ++++ | − | ++++ |
| *E. coli* extract containing pPT101 ATCC 53212 now 67854 | +++ | − | +++ |
| *E. coli* extract containing PEMBL8 | − | − | − |

0.1 ng of the purified *pertussis* toxin was used as a positive control. The sample was constituted by 5 μl of *E. coli* lysate containing the plasmid PT101. The negative control was constituted by the same strain of *E. coli* containing the plasmid used as a vector, without the genes for the *pertussis* toxin (pEMBL8).

It may be seen from table 2 that the extract of cells of *E. coli* (pPT101) ATCC 67854 gave a positive result and the toxin could be neutralized by anti-*pertussis* toxin antibodies but not by antibodies from the same goat before it had been immunized.

The strain *E. coli* JM 101 (pEMBL8) did not have any activity in this test.

We may thus conclude that the fragment of Eco RI chromosomal DNA with 4696 base pairs cloned by us in the plasmid pEMBL8 is able to synthesize a toxin which is functionally identical to the *pertussis* toxin produced by *B. pertussis* BP165 and the *pertussis* toxin can be neutralised by antibodies for the toxin itself.

EXAMPLE 10

Expression and Purification of the 5 Subunits of the *pertussis* Toxin a) Expression of the 5 Subunits The hybrid plasmids PTE255 (S1), PTE211 (S2), PTE 221 (S3), PTE240 (S4) and PTE230 (S5) constructed as described in the examples 4 to 8 were introduced by transformation of the strain of *E. coli* K12 H1 trp.

Each of the transformed strains was then grown in 10 ml of LB medium at 30° C. for one night. At the end of this period, the 10 ml of each culture were added to 400 ml of fresh LB medium in two-liter flasks.

The flasks were kept under agitation at 30° C. for two hours and at a temperature of 42° C. for 2.5 hours.

The cultures were centrifuged and the cells separated and resuspended in 3 ml of 25% sucrose, 10 ml Tris-HCl (pH 8.0), 1 mM EDTA.

5 μl of each of the said cultures then had added to it 80 μl of lysis buffer (4% SDS, 125 mM Tris (pH 6.8), 10% B-mercaptoethanol, 10% glycerol and 0.02% bromophenol blue, they were brought to boiling point for five minutes and then loaded onto a 15% polyacrylamide gel.

The proteins were then subjected to electrophoresis at 25 milliamps for five hours and the gel coloured and decoloured as reported by Laemli (Nature, 227, 680-85, 1970).

FIG. 10A shows the electrophoresis of the total lysate of the strains which produce the polymerase of MS2 (A) and the 5 unpurified subunits (S1-S5) fused to this.

b) Purification of the 5 Subunits

The cells of each of the said cultures were resuspended in 3.2 ml of 2.5% sucrose solution, 0.1 ml of lysozyme (40 mg/ml) and 0.8 ml of 0.5M EDTA was added and they were incubated at 37° C. for 30 minutes.

At the end of this period, to each of the suspensions were added 8 ml of lysis buffer (1% Triton ×100, 50 mM Tris pH 6.00, 63 mM EDTA) and then they were kept at 0° C. for 15 minutes and at 37° C. for 30 minutes.

Subsequently the cells were subjected to sonic disruption and centrifuged at 10000 revolutions for 10 minutes.

The precipitate thus separated was resuspended in 5 ml of 1M urea, kept at 37° C. for 30 minutes, centrifuged and, after separation of the supernatant liquid, resuspended in 5 ml of 7M urea. Thus partial purification of the subunits produced was obtained as given in FIG. 10B.

The partially-purified proteins were resuspended again in 5 ml of 7M urea, loaded on to a preparative polyacrylamide gel (3 mm×50 cm) and subjected to electrophoresis at 50 milliamps for 8 hours.

After colourating, the band containing the fusion protein was cut and electroeluted at 200 volts for 48 hours in a dialysis bag.

The electroeluted protein was then dialyzed against distilled water and precipitated by the addition of 9 volumes of acetone.

The protein was then recovered by centrifuging and resuspended in 0.1M $NaHCO_3$.

FIG. 10C shows the results obtained for the individual purified proteins.

Preparation of the Sera against the 5 Subunits

The purified, fused proteins (S1, S2, S3, S4 and S5) obtained as indicated in Example 10 above were used to immunize rabbits in accordance with the following scheme:

Day 1: 1 ml of solution containing about 1 mg of the fused protein was mixed with 1 ml of whole Freund adjuvant and injected subcutaneously into a rabbit.

Day 18: The treatment of Day 1 was repeated with the use of incomplete adjuvant.

Day 27: 1 ml of a solution with a protein content of about 1 mg was injected intravenously.

Day 37: The rabbits were bled and the serum recovered.

The anti-sera to the 5 subunits thus prepared were then tested by the Western Blot technique to check whether they recognized the five natural proteins.

About 100 mg of the purified *pertussis* toxin indicated in Example 1 was loaded on to a 15% polyacrylamide gel and subjected to electrophoresis.

The subunits thus separated were then transferred on to nitrocellulose by electro-blotting.

The sheet of nitrocellulose containing the subunits was cut vertically into a number of identical strips each of which was subsequently analyzed by the Western blot technique.

In practice, the strips of nitrocellulose were suspended in PBS 0.15M NaCl, 10 mM phosphates pH 7.4 containing 1×Denhart (0.03% bovine albumin, 0.02% FiColl 70 and 0.02% polyvinyl pyrrolidone) and 0.05% Tween for two hours and were washed two times, for 3 minutes each time, with PBS containing 0.05% of Tween 20.

They were subsequently incubated for one night at ambient temperature with a 1/100 dilution of the desired serum in PBS with the addition of 0.05% Tween 20.

They were then washed three times for 15 minutes each time, with a solution of 10 mM Tris, 0.9% NaCl and 0.1% Tween 20 (TBS) incubated with a conjugate of gammaglobulin anti-globulin of goat-peroxidate or globulin anti-globulin of rabbit peroxidase (Miles) diluted 1/100 in TBS and finally washed 3 times in TBS and one in Tris 0.01M (pH 6.8) for 10 minutes. To each of the solutions was then added the substrate for the peroxidase: 20 mL Tris 0.05M pH 6.8, 5 ml 0.3% 4-chloro 1 naphthol in methanol and 7 μl of $H_2O_2$.

The reaction was stopped by washing the filters in distilled water.

The results given in FIG. 11 show that the fused proteins obtained with the use of the genes which code for the five subunits of PT, when injected into rabbits, induce the formation of specific antibodies capable of recognizing each of the subunits of the natural toxin.

EXAMPLE 12

Analysis of the Enzymatic Activity of the Fused Protein S1

10 μl of fused protein S1 and 10 μl of PT preincubated with 25 mM of dithiothreitol at ambient temperature for 30 minutes were added to a solution containing 10 μl of homogenized ox retina (ROS), 80 μl of $H_2O$, 5 μl of Tris 2M (pH7.5) 1 μl of ATP 100 mM, 1 μl of GTP 10 mM, 10 μl of thymidine and 1 μl (1 μCi) of $^{32}P$ NAD.

The mixture was kept at ambient temperature for 30 minutes, centrifuged, the supernatant was separated and the precipitate containing the ROS was dissolved in sodium dodecylsulphate loading buffer, loaded on to 15% polyacrylamide gel and subjected to a potential difference of 125 volts for 5 hours.

At the end of this period, the gel was dried and subjected to autoradiography.

The results (FIG. 12) show that: lane A) the *pertussis* toxin (PT) ADP ribosyles the transducin, lane B) in the absence of the *pertussis* toxin this is not marked and lane C) the fused electroeluted S1 has the same ADP ribosylating activity as PT.

EXAMPLE 13

Cloning, Sequence and Expression of the Genes of *Bordetella bronchiseptica* and *Bordetella parapertussis*

Although *B. bronchiseptica* and *B. pertussis* do not produce active *pertussis* toxin, we have found that they contain the coding genes for this. By operating as described in Examples 2, 3 and 4, we have cloned and sequenced the genes of *Bordetella bronchiseptica* (ATCC 4617) and *Bordetella parapertussis* (ATCC 9305) which code for the five subunits of the *pertussis* toxin.

The nucleotide sequence obtained, given in FIG. 13, shows that there are small differences between the three strains. One of these lacks the Eco RI site at 4696 and hence the genes of *B. bronchiseptica* and *B. parapertussis* are contained in Eco RI fragments with 4935 bp instead of 4696. This difference in dimensions may be used as a diagnostic criterion for distinguishing *B. pertussis* from *B. parapertussis* and *B. bronchiseptica*, in the following manner: Bordetella chromosomal DNA was digested with Eco RI on an agarose gel, transferred on to nitrocellulose and hybridized by the techniques described for the plasmid PPT 101 and its fragments of cloned DNA.

Figure 14:
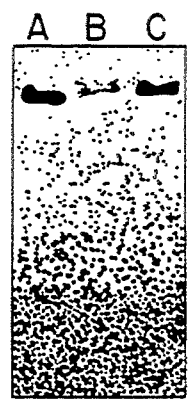

The results of the autoradiography enable the *B. pertussis* to be distinguished from the *B. parapertussis* and *bronchiseptica* which hybridize in a higher molecular weight band (FIG. 14).

FIG. 15 gives the amino acid sequences deduced from the five subunits in the three species of Bordetella. As may be seen, there are several changes of amino acids. To check whether these changes alter the function and immunogenicity of the subunits, operating as described in Example 4, we have expressed the genes which code for the subunit S1 of *B. bronchiseptica* and *parapertussis*. The fused proteins obtained were immunogenically similar to those of *B. pertussis* and in fact were recognized in Western blot by antitoxin antibodies of *pertussis*.

Figure 16:
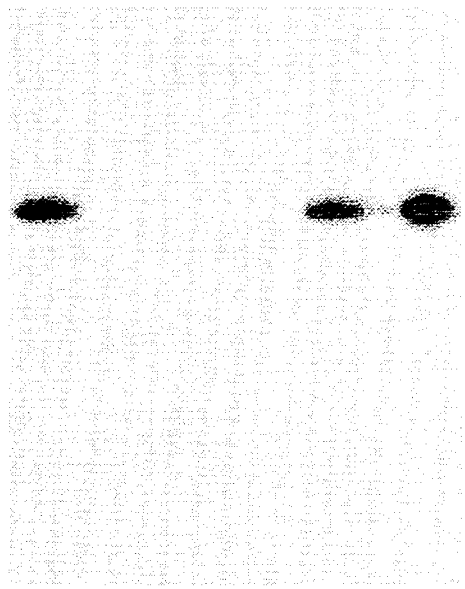

Moreover, by operating as described in Example 12, we found that both the proteins had the same enzymatic activity as the subunit S1 of *B. pertussis* (FIG. 16). This example shows that the proteins with the sequence given in FIG. 15 although containing several variations, may be used as a vaccine against *pertussis*.

We claim:

1. Composition for the stimulation of protection against infections of *Bordetella pertussis* including at least an effective quantity of *pertussis* toxin obtained by chemical synthesis or from microorganisms transformed with molecules of recombinant DNA containing the five genes that code for *pertussis* toxin.

2. In the process for the preparation of anti-*pertussis* vaccine containing detoxified *pertussis* toxin, the improvement which consists in substituting for said *pertussis* toxin the *pertussis* toxin obtained by the growth of a micro-organism transformed by a hybrid plasmid obtained by the union of an expression vector and a cloned and sequenced Eco RI fragment of *Bordetella pertussis* chromosomal DNA with 4696 base pairs containing the genes which code for the five subunits of the *pertussis* toxin, comprising the sequence given in FIGS. 3 and 13.

3. The process of claim 2 wherein said Eco RI fragment or said further fragments are placed under the control of the regions with the hybrid plasmid which regulate their expression.

4. The process of claim 3 wherein said hybrid plasmid in pPT101 in which the Eco RI fragment is inserted in the Eco RI restriction site of pEMBL8.

5. The process of claim 2 wherein the transformed micro-organism is *Escherichia coli*.

6. The process of claim 5 wherein the transformed micro-organism is ATCC 67854.

* * * * *

UNITED STATES PATENT AND TRADEMARK OFFICE
CERTIFICATE OF CORRECTION

PATENT NO. : 5,427,788
DATED : June 27, 1995
INVENTOR(S) : Rino Rappuoli, Alfredo Nicosia, Maria B. Arico It is certified that error appears in the above-indentified patent and that said Letters Patent is hereby corrected as shown below:

In Column 1, at line 4, change "division" to --continuation--; at lines 5-6, change "continuation" to --division--; at lines 6-7, delete "now abandoned,".

Signed and Sealed this

Fifteenth Day of April, 1997

Attest:

BRUCE LEHMAN

Attesting Officer    Commissioner of Patents and Trademarks